United States Patent
Gysling

(10) Patent No.: US 7,437,946 B2
(45) Date of Patent: Oct. 21, 2008

(54) APPARATUS AND METHOD FOR MEASURING A PARAMETER OF A MULTIPHASE FLOW

(75) Inventor: Daniel L. Gysling, Glastonbury, CT (US)

(73) Assignee: CiDRA Corporation, Wallingford, CT (US)

( * ) Notice: Subject to any disclaimer, the term of this patent is extended or adjusted under 35 U.S.C. 154(b) by 152 days.

(21) Appl. No.: 11/442,954

(22) Filed: May 30, 2006

(65) Prior Publication Data

US 2007/0001028 A1    Jan. 4, 2007

Related U.S. Application Data

(60) Provisional application No. 60/685,532, filed on May 27, 2005, provisional application No. 60/736,684, filed on Nov. 14, 2005.

(51) Int. Cl.
*G01F 1/22* (2006.01)
(52) U.S. Cl. .................................................. 73/861.23
(58) Field of Classification Search .............. 73/861.23, 73/861.28
See application file for complete search history.

(56) References Cited

U.S. PATENT DOCUMENTS

| | | | |
|---|---|---|---|
| 2,874,568 A | 2/1959 | Petermann | 73/861.02 |
| 3,715,709 A | 2/1973 | Zacharias et al. | 367/95 |
| 3,751,979 A | 8/1973 | Ims | 73/861.27 |
| 3,781,895 A | 12/1973 | Monser | 343/708 |
| 3,851,521 A | 12/1974 | Ottenstein | 73/40.5 |
| 3,885,432 A | 5/1975 | Herzl | 73/861.22 |
| 3,952,578 A | 4/1976 | Jacobs | 73/64.1 |
| 4,004,461 A | 1/1977 | Lynnworth | 73/861.27 |
| 4,032,259 A | 6/1977 | Brown | 417/43 |
| 4,048,853 A | 9/1977 | Smith et al. | 73/861.25 |
| 4,080,837 A | 3/1978 | Alexander et al. | 73/61.45 |
| 4,195,517 A | 4/1980 | Kalinoski et al. | 73/461.27 |

(Continued)

FOREIGN PATENT DOCUMENTS

DE    4306119    9/1994

(Continued)

OTHER PUBLICATIONS

Sonar-Based Volumetric Flow Meter For Pulp and Paper Applications—Daniel L. Gysling & Douglas H. Loose—Dec. 13, 2003.

(Continued)

*Primary Examiner*—Jewel V Thompson

(57) ABSTRACT

An apparatus for determining a characteristic of an aerated fluid flowing within a pipe is provided and includes at least one first sensing device associated with the pipe, such that the at least one first sensing device senses a low-frequency component of the aerated fluid flow and generates first sensor data responsive to the low-frequency component of the aerated fluid. At least one second sensing device is also included and is associated with the pipe such that the at least one second sensing device senses a high-frequency component of the aerated fluid flow and generates second sensor data responsive to the high-frequency component of the aerated fluid. Furthermore, a processing device is included and is communicated with the at least one first sensing device and the at least one second sensing device to receive and process the first sensor data and the second sensor data to generate fluid data.

23 Claims, 13 Drawing Sheets

U.S. PATENT DOCUMENTS

| | | | |
|---|---|---|---|
| 4,248,085 A | 2/1981 | Coulthard | 73/861.06 |
| 4,320,659 A | 3/1982 | Lynnworth et al. | 73/589 |
| 4,445,389 A | 5/1984 | Potzick et al. | 73/861.27 |
| 4,520,320 A | 5/1985 | Potzick et al. | 328/133 |
| 4,561,310 A | 12/1985 | Barnard et al. | 73/861.02 |
| 4,677,305 A | 6/1987 | Ellinger | 73/290 V |
| 4,717,159 A | 1/1988 | Alston et al. | 330/129 |
| 4,896,540 A | 1/1990 | Shakkottai et al. | 73/861.02 |
| 4,932,262 A | 6/1990 | Wlodarczyk | 250/227.3 |
| 5,040,415 A | 8/1991 | Barkhoudarian | 73/861.03 |
| 5,060,506 A | 10/1991 | Douglas | 73/24.01 |
| 5,083,452 A | 1/1992 | Hope | 73/61 R |
| 5,218,197 A | 6/1993 | Carroll | 250/227.19 |
| 5,285,675 A | 2/1994 | Colgate et al. | 73/23.2 |
| 5,289,726 A | 3/1994 | Miau et al. | 73/861.22 |
| 5,359,897 A | 11/1994 | Hamstead et al. | 73/597 |
| 5,363,342 A | 11/1994 | Layton et al. | 367/149 |
| 5,367,911 A | 11/1994 | Jewell et al. | 73/861.08 |
| 5,398,542 A | 3/1995 | Vasbinder | 73/40.5 |
| 5,415,048 A | 5/1995 | Diatschenko et al. | |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,625,140 A | 4/1997 | Cadet et al. | 73/24.01 |
| 5,708,211 A | 1/1998 | Jepson et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,856,622 A | 1/1999 | Yamamoto et al. | 73/861.28 |
| 5,948,959 A | 9/1999 | Peloquin | 73/1.83 |
| 6,016,702 A | 1/2000 | Maron | 73/705 |
| 6,151,958 A | 11/2000 | Letton et al. | 73/61.79 |
| 6,202,494 B1 | 3/2001 | Riebel et al. | 73/861.29 |
| 6,233,374 B1 | 5/2001 | Ogle et al. | 385/13 |
| 6,261,232 B1 | 7/2001 | Yokosawa et al. | 600/443 |
| 6,345,539 B1 | 2/2002 | Rawes et al. | 73/861.27 |
| 6,349,599 B1 | 2/2002 | Lynnworth et al. | 73/644 |
| 6,354,147 B1 | 3/2002 | Gysling et al. | 73/61.79 |
| 6,378,357 B1 | 4/2002 | Han et al. | 73/54.41 |
| 6,397,683 B1 | 6/2002 | Hagenmeyer et al. | 73/861.18 |
| 6,412,353 B1 | 7/2002 | Kleven et al. | 73/861.22 |
| 6,435,030 B1 | 8/2002 | Gysling et al. | 73/587 |
| 6,442,996 B1 | 9/2002 | Thurston et al. | 73/24.01 |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,959,604 B2 | 2/2003 | Davis et al. | |
| 6,532,827 B1 | 3/2003 | Ohnishi | 73/861.27 |
| 6,536,291 B1 | 3/2003 | Gysling et al. | 73/861.42 |
| 6,550,342 B2 | 4/2003 | Croteau et al. | 73/800 |
| 6,558,036 B2 | 5/2003 | Gysling et al. | 374/147 |
| 6,575,043 B1 | 6/2003 | Huang et al. | 73/861.18 |
| 6,587,798 B2 | 7/2003 | Kersey et al. | 702/50 |
| 6,601,005 B1 | 7/2003 | Eryurek et al. | 702/104 |
| 6,601,458 B1 | 8/2003 | Gysling et al. | 73/861.04 |
| 6,609,069 B2 | 8/2003 | Gysling | 702/48 |
| 6,658,945 B1 | 12/2003 | Kleven | 73/861.22 |
| 6,672,163 B2 | 1/2004 | Han et al. | 73/597 |
| 6,691,584 B2 | 2/2004 | Gysling et al. | 73/861.42 |
| 6,698,297 B2 | 3/2004 | Gysling | 73/861.63 |
| 6,732,575 B2 | 5/2004 | Gysling et al. | 73/61.79 |
| 6,773,603 B2 | 8/2004 | Moorehead et al. | 210/704 |
| 6,782,150 B2 | 8/2004 | Davis et al. | 385/12 |
| 6,813,962 B2 | 11/2004 | Gysling et al. | 73/861.26 |
| 6,837,098 B2 | 1/2005 | Gysling et al. | 73/61.79 |
| 6,837,332 B1 | 1/2005 | Rodney | 181/105 |
| 6,862,920 B2 | 3/2005 | Gysling et al. | 73/61.79 |
| 6,889,562 B2 | 5/2005 | Gysling et al. | |
| 6,898,541 B2 | 5/2005 | Gysling et al. | 902/100 |
| 6,971,259 B2 | 12/2005 | Gysling | |
| 6,988,411 B2 | 1/2006 | Gysling et al. | |
| 6,991,584 B2 | 1/2006 | Cowan | 73/861.42 |
| 7,032,432 B2 | 4/2006 | Gysling et al. | |
| 7,058,549 B2 | 6/2006 | Gysling et al. | |
| 7,062,976 B2 | 6/2006 | Gysling et al. | |
| 7,086,278 B2 | 8/2006 | Gysling et al. | |
| 7,096,719 B2 | 8/2006 | Gysling | |
| 7,110,893 B2 | 9/2006 | Davis et al. | |
| 7,121,152 B2 | 10/2006 | Currey et al. | |
| 7,127,360 B2 | 10/2006 | Davis et al. | |
| 7,134,320 B2 | 11/2006 | Banach et al. | |
| 7,139,667 B2 | 11/2006 | Gysling et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0006409 A1 | 1/2004 | Liljenberg et al. | |
| 2004/0011141 A1 | 1/2004 | Lynworth | |
| 2004/0016284 A1 | 1/2004 | Gysling et al. | |
| 2004/0069069 A1 | 4/2004 | Gysling et al. | |
| 2004/0074312 A1 | 4/2004 | Gysling | |
| 2004/0144182 A1 | 7/2004 | Gysling et al. | |
| 2004/0167735 A1 | 8/2004 | Rothman et al. | |
| 2004/0168522 A1 | 9/2004 | Bailey et al. | |
| 2004/0168523 A1 | 9/2004 | Bailey et al. | |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0000289 A1 | 1/2005 | Gysling et al. | |
| 2005/0005711 A1 | 1/2005 | Gysling et al. | |
| 2005/0005712 A1 | 1/2005 | Gysling et al. | |
| 2005/0005713 A1 | 1/2005 | Winston et al. | |
| 2005/0005912 A1 | 1/2005 | Gysling et al. | |
| 2005/0011258 A1 | 1/2005 | Gysling et al. | |
| 2005/0011283 A1 | 1/2005 | Gysling et al. | |
| 2005/0011284 A1 | 1/2005 | Davis et al. | |
| 2005/0012935 A1 | 1/2005 | Kersey | |
| 2005/0033545 A1 | 2/2005 | Gysling | |
| 2005/0039520 A1 | 2/2005 | Davis et al. | |
| 2005/0044929 A1 | 3/2005 | Gysling et al. | |
| 2005/0044966 A1 | 3/2005 | Gysling et al. | |
| 2005/0050956 A1 | 3/2005 | Gysling et al. | |
| 2005/0061060 A1 | 3/2005 | Banach et al. | |
| 2005/0072216 A1 | 4/2005 | Engel | |
| 2005/0125166 A1 | 6/2005 | Loose et al. | |
| 2005/0125170 A1 | 6/2005 | Gysling et al. | |
| 2005/0159904 A1 | 7/2005 | Loose et al. | |
| 2005/0171710 A1 | 8/2005 | Gysling et al. | |
| 2005/0246111 A1 | 11/2005 | Gysling et al. | |
| 2006/0037385 A1 | 2/2006 | Gysling | |
| 2006/0048583 A1 | 3/2006 | Gysling | |
| 2006/0053809 A1 | 3/2006 | Gysling et al. | |
| 2006/0169058 A1 | 8/2006 | Gysling | |
| 2006/0212231 A1 | 9/2006 | Bailey | |
| 2006/0266127 A1 | 11/2006 | Gysling et al. | |
| 2007/0005272 A1 | 1/2007 | Gysling | |
| 2007/0157737 A1 * | 7/2007 | Gysling et al. | 73/861.23 |

FOREIGN PATENT DOCUMENTS

| | | |
|---|---|---|
| EP | 0290336 | 11/1988 |
| EP | 1186868 | 3/2002 |
| GB | 2210169 | 6/1989 |
| GB | 226807 | 10/2002 |
| WO | WO 93/14382 | 7/1993 |
| WO | WO 99/067629 | 12/1999 |

| | | |
|---|---|---|
| WO | WO 99/67629 | 12/1999 |
| WO | WO 00/00793 | 1/2000 |
| WO | WO 0000793 | 1/2000 |
| WO | WO 00/46583 | 8/2000 |
| WO | WO 01/02810 | 1/2001 |
| WO | WO 01/069040 | 9/2001 |
| WO | WO 02/50511 | 6/2002 |
| WO | WO 2004/063741 | 7/2004 |

OTHER PUBLICATIONS

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

SONAR Gets into the Flow—Daniel L. Gysling and Douglas H. Loose—Modern Process—Jan. 2004.

Piezo Film Sensors Technical Manual—Measurement Specialties Inc.—Sensor Products Division Apr. 2, 1999.

U.S. Appl. No. 11/268,815, filed Nov. 2005, Gysling et al.

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research, The Parametric Approach", H. Krim and M. Viberg, IEEE Signal Processing Magazine, Jul., 1996, pp. 67-94.

"Development of an array of pressure sensors with PVDF film, Experiments in Fluids 26", Jan. 8, 1999, Springer-Verlag.

"Viscous Attenuation of Acoustic Waves in Suspension" by R.L. Gibson, Jr. and M.N. Toksoz.

Acoustic definition, Retrieved from the internet http://www.m-2.com/dictionary/acoustic>.

"Flow Velocity Measurement using Spatial Filter" Yoshio Kurita, Takaharu Matsumoto, Yukitake Shibata—Nov. 1979.

* cited by examiner

US 7,437,946 B2

APPARATUS AND METHOD FOR MEASURING A PARAMETER OF A MULTIPHASE FLOW

CROSS-REFERENCE TO RELATED PATENT APPLICATIONS

This application claims the benefit of U.S. Provisional Application No. 60/685,532 filed May 27, 2005; and U.S. Provisional Application No. 60/736,684, filed Nov. 14, 2005, which are incorporated herein by reference in their entirety.

TECHNICAL FIELD

This invention relates to an apparatus for measuring a parameter of a process flow passing within a pipe, and more particularly to a flow measurement apparatus having ultrasonic sensors and an array of strain-based sensors and for processing data signals therefrom to provide an output indicative of the speed of sound propagating through the process flow and/or a flow parameter of the process flow passing through a pipe.

BACKGROUND ART

In fields involving flowing fluids for industrial applications, such as slurries, liquids, chemical, paper, pulp, petroleum, gas, pharmaceutical, food, mining, minerals and vapors and gasses in refinery, it is sometimes beneficial to know certain characteristics of the flowing fluids. For example, in the petroleum industry in which billions of dollars of crude oil are fiscally measured each day on its way from the well heads to the refineries, the volumetric flow rate is a critical measurement in process control and optimization. Unfortunately however, large amounts of hydrocarbons tend to be present in crude oil and as such, during transport between the well heads and refineries the crude oil has a propensity to 'out gas' during transport resulting in small, unknown levels of entrained gases being present at fiscal measurement locations. This is undesirable for at least two (2) reasons.

First, because the effect of entrained gases on most known liquid volumetric technologies results in an over reporting of the liquid component flow rate by an amount equal to the volume of the entrained gases, the measured volumetric flow rate is typically inaccurate. In fact, standards have been imposed for volumetric flow. Unfortunately, however, while most standards for fiscal volumetric flow of liquids require that the liquid be completely devoid of gases, a problem arises when it becomes impractical to ensure that the liquid stream in question is indeed completely devoid of free gases. This is because although the gas volume fraction (GVF) level is typically less than 1%, it is often the primary source of error in fiscal measurement. Second, because the complete separation of the gas and liquid phases cannot be ensured, the liquid volume determination is also typically inaccurate resulting in an inaccurate water cut value. Thus, it is reasonable to expect that the more characteristics that are known about the flowing fluid, the better chance there is of effectively measuring, controlling, and optimizing the processing of the flowing fluid.

Accuracy of oil production measurement is typically limited to three constraints. One constraint is the inability to ensure complete separation of gas and liquid flow. This constraint results in inaccurate liquid volume determination, inaccurate gas volume determination, and inaccurate watercut determination. The second constraint is the relatively low number of flow measurements. This is not only due to the installation and maintenance requirements for each measurement device, but also to the affect each measurement device has on the fluid flow, such as an associated pressure drop. As such, increasing the number of measurement points causes a corresponding increase in the total associated pressure drop as well as an increase in the number and costs of installation and maintenance requirements. The reason is maintenance requirements, installation requirements and pressure drop in the point with any increase in measurement points. The third constraint is the very low number of watercut measurement points. This low number is due to the reliability of watercut measurement devices and the calibration requirements of the meters.

Thus, it would be advantageous, particularly in the oil and production field, to have a reliable, non-intrusive, clamp-on apparatus capable of measuring the parameters of an aerated multiphase fluid flow, such as the volumetric flow rate of the liquid of the process flow, the gas volume (or void) fraction of the flow, the watercut of the flow, and the volumetric flow rate of each of the phases of the flow. The present invention provides such an apparatus.

SUMMARY OF THE INVENTION

An apparatus for determining a characteristic of an aerated fluid flowing within a pipe is provided, wherein the device includes at least one first sensing device. The at least one first sensing device is associated with the pipe, such that the at least one first sensing device senses a low-frequency component of the aerated fluid flow and generates first sensor data responsive to the low-frequency component of the aerated fluid. Additionally, at least one second sensing device is provided, wherein the at least one second sensing device is associated with the pipe such that the at least one second sensing device senses a high-frequency component of the aerated fluid flow, wherein second sensor data is generated responsive to the high-frequency component of the aerated fluid. Moreover, a processing device is provided, wherein the processing device is communicated with the at least one first sensing device and the at least one second sensing device to receive and process the first sensor data and the second sensor data to generate fluid data responsive to a characteristic of the aerated fluid flow.

A method for determining a characteristic of a fluid flowing within a pipe is provided, wherein the method includes generating Speed of Sound data responsive to the speed of sound within at least a portion of the fluid for at least one of a first frequency and a second frequency, sensing the convective velocity of pressure fields created by the fluid and generating convective data responsive to the convective velocity of the pressure fields. Additionally, the method includes processing the Speed of Sound data and the convective data to determine the characteristic of the fluid.

An apparatus for determining the water cut value of a multiphase fluid flowing within a pipe is provided, wherein the device includes a transmitting device configured to introduce a high-frequency acoustic signal into the fluid, a receiving device, wherein the receiving device is configured to receive the high-frequency acoustic signal after the high-frequency acoustic signal has traversed at least a portion of the fluid, wherein at least one of the transmitting device and the receiving device generates sensor data responsive to the received high-frequency acoustic signal and a processing device, wherein the processing device is communicated with at least one of the transmitting device and the receiving device to receive and process the sensor data to determine the water cut value of the fluid.

A method for determining the water cut value of a fluid flowing through a pipe is provided, wherein the method includes introducing an acoustic wave having a predetermined frequency into the fluid, after the acoustic wave has traversed at least a portion of the fluid, receiving the acoustic wave and generating sensor data responsive at least in part to the received acoustic wave and processing the sensor data to determine the water cut value of the fluid The foregoing and other objects, features and advantages of the present invention will become more apparent in light of the following detailed description of exemplary embodiments thereof.

BRIEF DESCRIPTION OF THE DRAWINGS

FIG. 11 is a schematic diagram of a flow logic of an array processor of a flow measuring apparatus in accordance with the present invention.

BEST MODE FOR CARRYING OUT THE INVENTION

Figure 1:
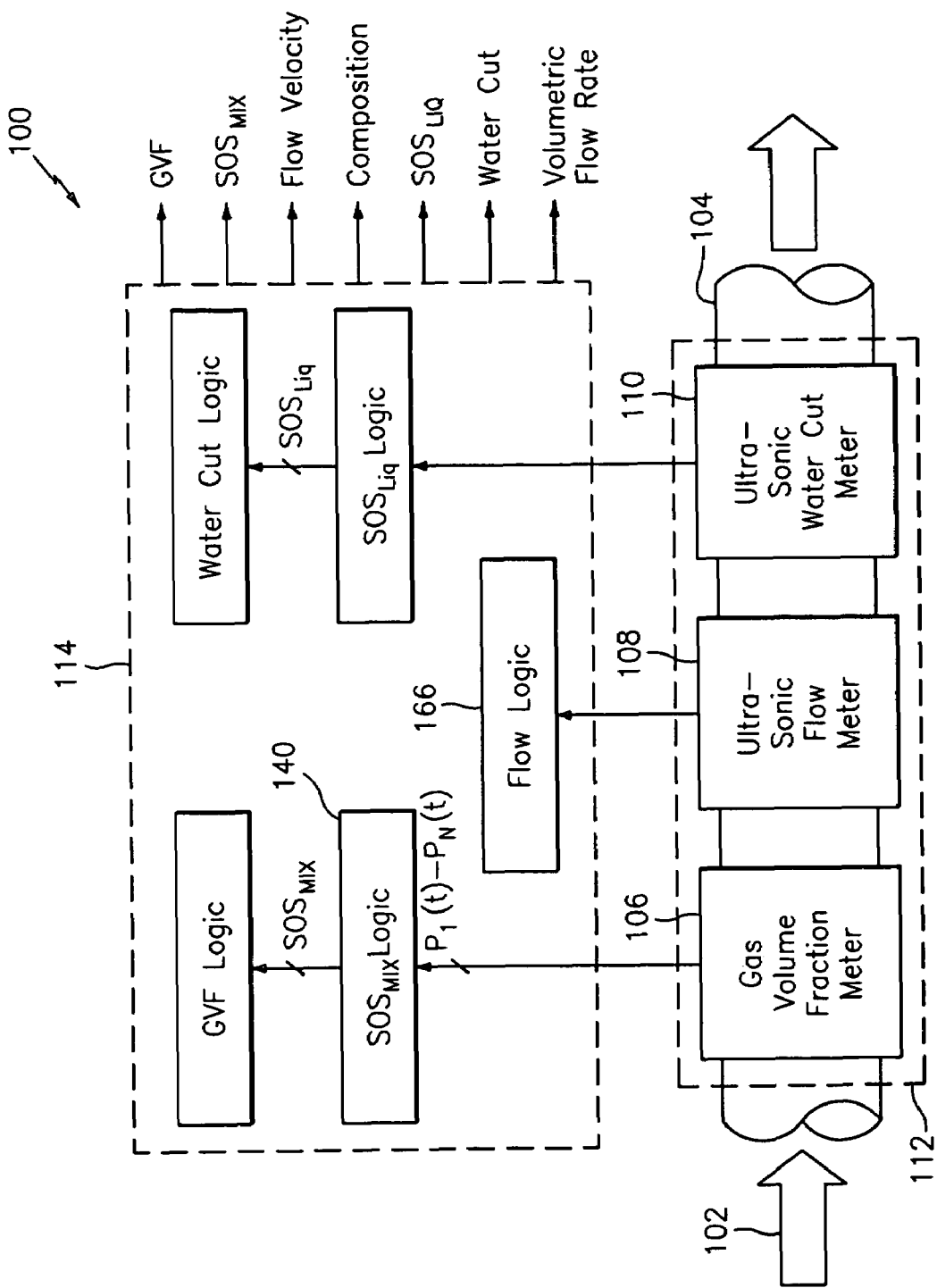
FIG. 1 is a block diagram of a flow measurement apparatus having an array of strain-based sensors and an array of ultrasonic sensors for measuring parameters of a multiphase flow in accordance with the present invention.

FIG. 1 illustrates a block diagram of a flow measurement device 100 for measuring a parameter of a multiphase flow 102 passing through a pipe 104. The multiphase flow or mixture 102 includes any mixture having any combination of a gas, liquid, or solid phase. While the present invention is particularly useful in measuring multiphase flows 102, the apparatus 100 can also measure a parameter of a single phase flow. As discussed hereinbefore, the apparatus 100 embodying the present invention is useful in measuring a multiphase flow 102 comprising oil, water and gas. The description of the present invention will therefore assume that the mixture is a combination of oil, water and gas, however, the invention contemplates that any single or multiphase flow 102 can be measured.

As shown in FIG. 1, the apparatus 100 functions as a gas volume fraction (or void fraction) meter 106, an ultrasonic flow meter 108, and an ultrasonic watercut meter 110. The gas volume fraction (GVF) meter 106 provides an output indicative of the gas volume fraction or void fraction of the mixture 102 by measuring the speed of sound propagating at low frequencies axially through the flow 102 in the pipe 104. The ultrasonic flow meter 108 provides a plurality of high frequency acoustic signals through the flow 102 to provide output signals indicative of pressure disturbances (e.g., vortical disturbances) or other disturbances or other characteristics of the flow that convect or propagate with the flow 102 past the ultrasonic sensors, which will be described in greater detail hereinafter. The ultrasonic watercut meter 110 measures the speed of sound of a high frequency signal propagating through the flow 102 to provide an output signal indicative of the speed of sound of the liquid component of the flow 102, which is indicative of the watercut of the mixture 102. Watercut is the phase fraction or percentage of the water in the liquid portion of the flow 102.

One can appreciate that the combination of the GVF meter 106, flow meter 108 and watercut meter 110 provides sufficient information to fully characterize the multiphase fluid 102 flowing through the pipe 104. Specifically, the apparatus 100 is capable of measuring at least the flow velocity, volumetric flow rate, flow composition (e.g., phase fraction of each phase of the fluid), watercut, volumetric flow rate of each phase of mixture 102, gas volume (void) fraction of the flow 102, speed of sound of the mixture 102 and the speed of sound of the liquid component of the flow 102. One can appreciate that these measured parameters are particularly important in oil production applications.

Figure 2:
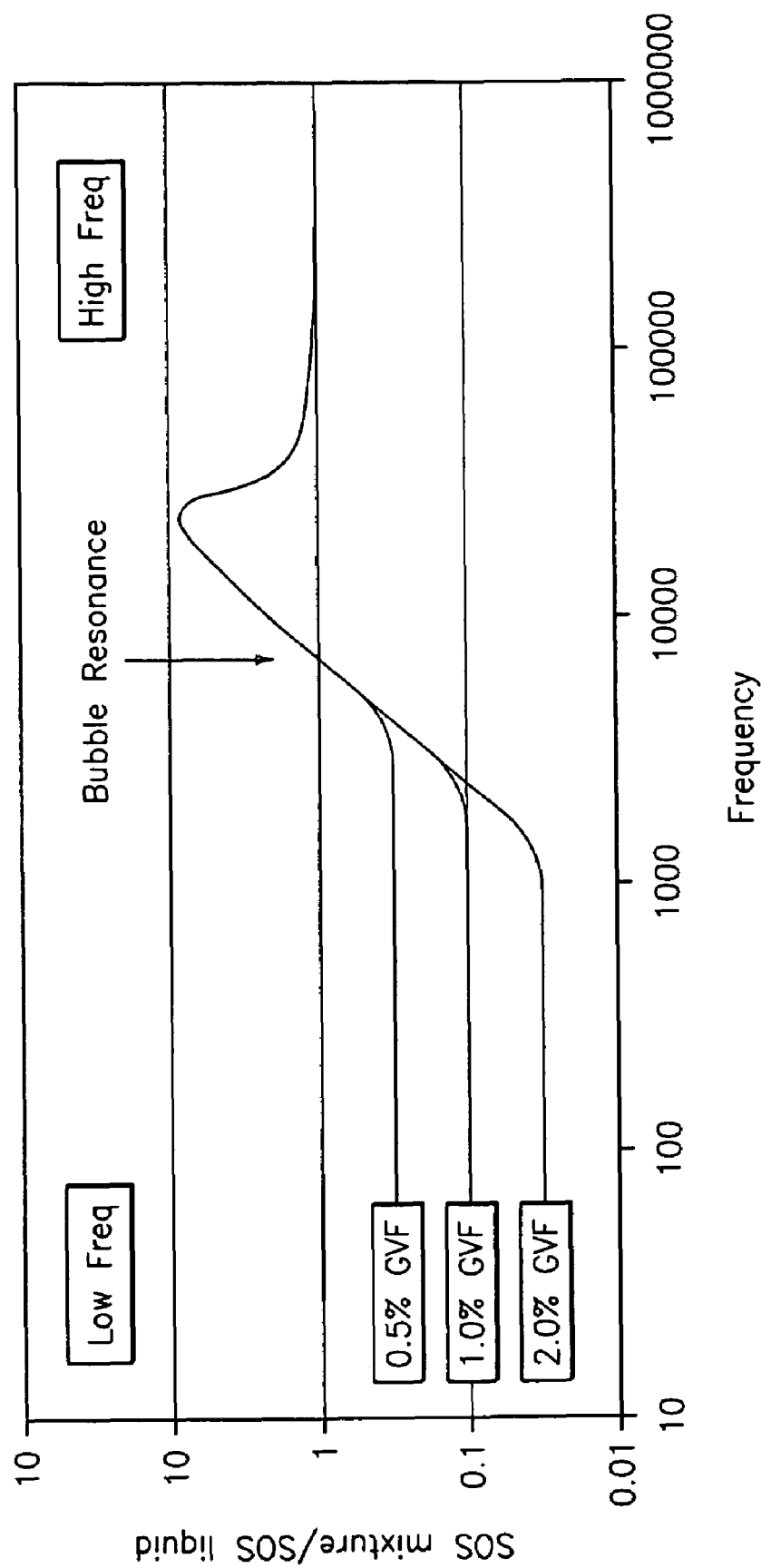
FIG. 2 is a plot of the measured speed of sound normalized to the speed of sound of the liquid over a frequency range in accordance with the present invention.

An important aspect of the present invention is the recognition that a frequency dependence of the speed of sound propagating through the fluid flow 102 exists for bubbly fluids. The bubble resonance determines the transition frequency. FIG. 2 illustrates the frequency dependence of the speed of sound in bubbly fluids. As shown, at low frequencies below the bubble resonant frequency (approximately 100 Hz to 1000 Hz), the speed of sound propagating through the fluid 102 is dramatically influenced by entrained gases. Conversely, at high frequencies above the bubble resonant frequency (approximately 1 MHz and greater), entrained gas in the fluid flow 102 has no significant impact on the speed of sound propagating through the liquid component of the flow 102. Recognizing this phenomenon, the apparatus 100 embodying the present invention provides a meter (i.e. GVF meter 106) to measure the speed of sound at low frequencies below the bubble resonant frequency, and another meter (i.e., ultrasonic watercut meter 108) to measure the speed of sound at high frequencies above the bubble resonant frequency.

As will be described in greater detail hereinafter, the measured speed of sound at the lower frequency (e.g., sub-resonant frequencies) is indicative of the speed of sound of the mixture 102, while the measured speed of sound at the higher frequencies (e.g., super-resonant frequencies) is indicative of the speed of sound of the liquid component of the mixture 102. Knowing the speed of sound of the mixture 102 enables the gas volume (and void) fraction of the flow 102 (or mixture) to be determined. Further, knowing the speed of sound of the liquid component of the mixture 102 enables the watercut to be determined. This processing will be described in greater detail hereinafter. Also, knowing the gas volume fraction (or void fraction) and the water cut, the phase fraction and the volumetric flow rate of each phase of the fluid flow 102 can be determined, as will be described in greater detail hereinafter.

Figure 3:
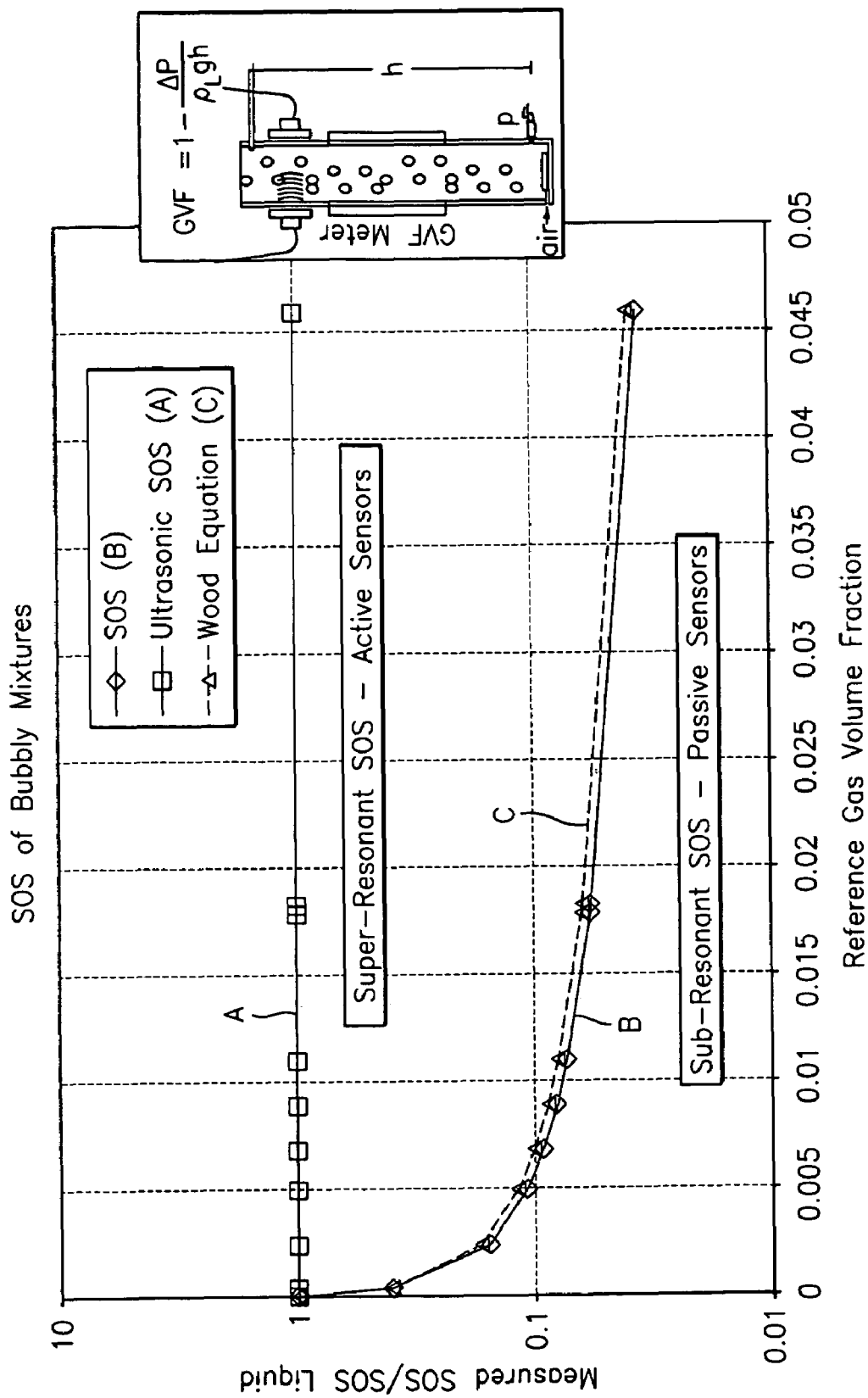
FIG. 3 is a plot of the measured speed of sound normalized to the speed of sound of the liquid as a function of gas volume fraction in accordance with the present invention.

Tests were performed using a vertical pipe filled with a fluid, wherein bubbles were injected into the fluid at the bottom of the pipe. Using an ultrasonic sensor and a GVF meter, the speed of sound at super-resonant frequencies and sub-resonant frequencies, respectively, were measured. The data is provided in FIG. 3, which illustrates the phenomenon described above that the measured speed of sound of the liquid component of the mixture 102 (e.g., super-resonant SOS) is not effected by the entrained gas, while the measured speed of sound of the mixture 102 (e.g., sub-resonant SOS) is effected by the entrained gas. FIG. 3 illustrates effects of the speed of sound of bubble mixtures or flows. Specifically, the measured speed of sound normalized by the liquid speed of sound is plotted as a function of the reference gas volume fraction.

The line A shows the normalized measured super-resonant speed of sound as a function of the referenced GVF. As discussed hereinbefore, the measured speed of sound at higher frequencies (super-resonant) is not affected by entrained gas and is indicative of the speed of sound of the liquid of the mixture 102 regardless of the amount of entrained gas.

The line B shows the normalized measured sub-resonant speed of sound as a function of the referenced GVF. As discussed hereinbefore, the measured sound speed at lower frequencies (sub-resonant) is affected by entrained gas by a known or determinable relationship, and thus enabling the determination of the gas volume (or void) fraction of the multiphase flow or mixture 102.

The line C shows the theoretical normalized sub-resonant speed of sound of the mixture 102 as a function of the referenced GVF in accordance with the Woods equation. As shown, the measured sub-resonant speed of sound correlated with the theoretical determination of the sub-resonant speed of sound.

Figure 4:
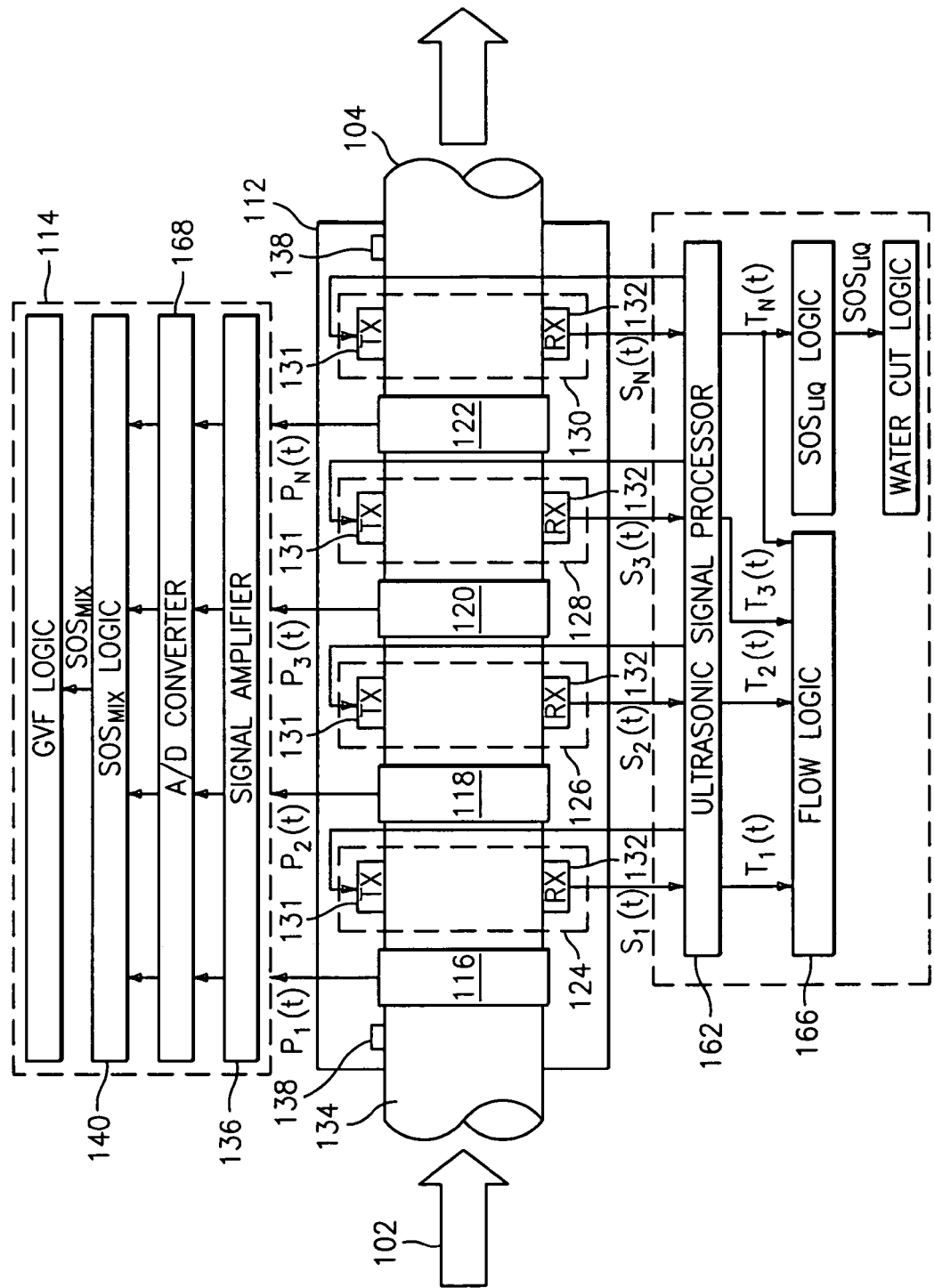
FIG. 4 is a schematic diagram of a flow measurement apparatus of FIG. 1 having an array of strain-based sensors and an array of ultrasonic sensors for measuring parameters of a multiphase flow.
Figure 5:
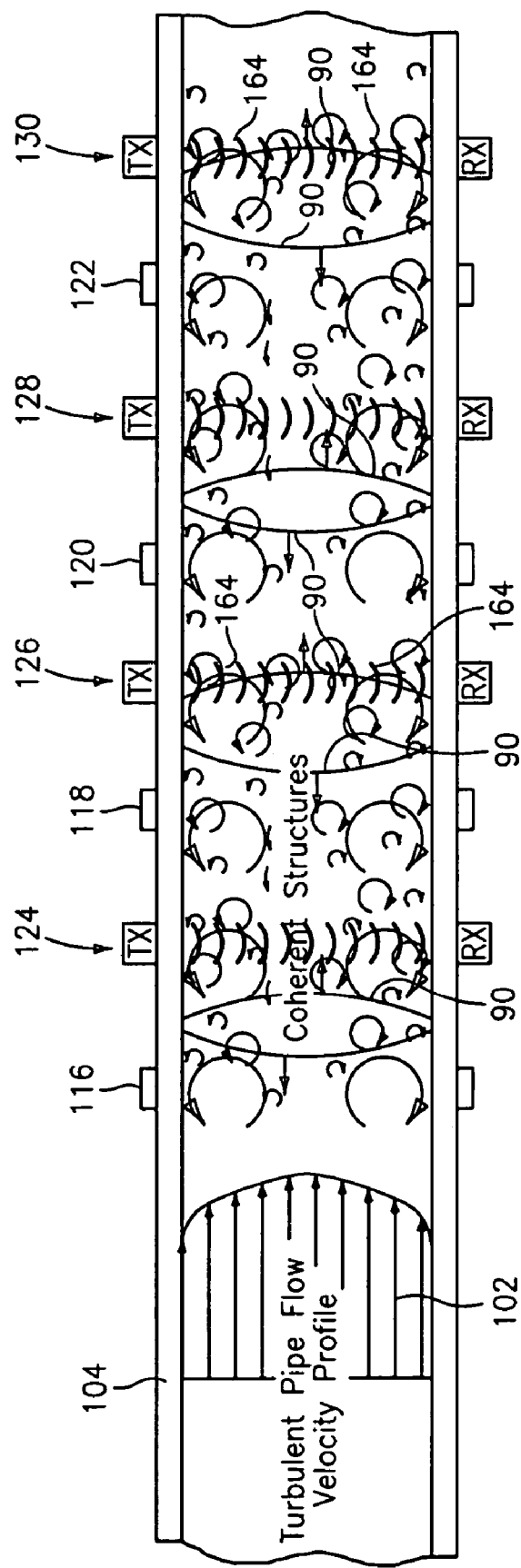
FIG. 5 is a cross-sectional view of a pipe having a turbulent fluid flow or mixture flowing therein, the flow having coherent structures therein, namely acoustic waves and vortical disturbances, in accordance with the present invention.

FIG. 4 illustrates a schematic diagram of the flow measurement apparatus 100 of FIG. 1 that includes a sensing device (sensor head) 112 mounted to the pipe 104 and a processing unit or array processor (transmitter) 114. The apparatus 100, in accordance with the present invention, can determine the speed at which sound (i.e., acoustic wave 90 in FIG. 5) propagates through the fluid flow 102 within the pipe 104 to measure particular characteristics of the single or multi-phase fluids 102. To simplify the explanation of the present invention, the flow 102 propagating through the pipe 104 will be referred to as a process flow 102 with the understanding that the fluid or process flow 102 may be a single phase or multi-phase flow, as described hereinbefore.

The sensing device 112 comprises an array of strain-based sensors or pressure sensors 116-122 for measuring the unsteady pressures produced by acoustic pressure disturbances (e.g., acoustic waves 90) within the pipe 104 to determine the speed of sound propagating through the flow 102. The sensing device 112 further includes an array of ultrasonic sensors 124-130, each of which having a transmitter 131 and a receiver 132, to also measure a parameter of the flow 102. The pressure sensors 116-122 and ultrasonic sensors 124-130 are shown interlaced, however, one should appreciate that each respective sensor array may be partially interlaced or not interlaced at all without departing from the scope of the present invention. It is also contemplated that the GVF meter 106 and the ultrasonic flow meter 108 may be two distinct units disposed adjacent to each other on the pipe 104.

The pressure signals $P_1(t)$-$P_N(t)$ and ultrasonic signals $S_1(t)$-$S_N(t)$ are provided to the processing unit 114, which digitizes the signals and computes the appropriate flow parameter(s). Although a cable is shown as electronically connecting the sensing device 112 to the processing unit 114, any method and/or device suitable to the desired end purpose may be used to communicate the sensing device 112 with the processing unit 114. The analog pressure sensor signals $P_1(t)$-$P_N(t)$ are typically 4-20 mA current loop signals.

The array of pressure sensors 116-122 comprises an array of at least two pressure sensors 116, 118 spaced axially along an outer surface 134 of the pipe 104, having the process flow 102 propagating therein. The pressure sensors 116-122 may be clamped onto or generally removably mounted to the pipe 104 by any releasable fastening device, such as magnetic fasteners, bolts, screws and/or clamps. Alternatively, the sensors may be permanently attached to or integral (e.g., embedded) with the pipe 104. The array of sensors of the sensing device 112 may include any number of pressure sensors 116-122 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow 102. Therefore, the number of sensors used is dependent at least on the degree of accuracy desired and the desire update rate of the output parameter provided by the apparatus 100. The pressure sensors 116-122 measure the unsteady pressures produced by acoustic waves propagating through the flow 102 within the pipe 104, which are indicative of the SOS propagating through the fluid flow 102 in the pipe 104. The output signals ($P_1(t)$-$P_N(t)$) of the pressure sensors 116-122 are provided to a signal amplifier 136 that amplifies the signals generated by the pressure sensors 116-122. The processing unit 114 processes the pressure measurement data $P_1(t)$-$P_N(t)$ and determines the desired parameters and characteristics of the flow 102, as described hereinbefore.

The apparatus 100 also contemplates providing one or more acoustic sources 138 to enable the measurement of the speed of sound propagating through the flow 102 for instances of acoustically quiet flow 102. The acoustic source(s) 138 may be a device that taps or vibrates on the wall of the pipe 104, for example. The acoustic sources 138 may be disposed at the input end or the output end of the array of sensors 116-122, or at both ends as shown. One should appreciate that in most instances the acoustic sources 138 are not necessary and that the apparatus 110 passively detects the acoustic ridge provided in the flow 102, as will be described in greater detail hereinafter. The passive noise includes noise generated by pumps, valves, motors, and the turbulent mixture 102 itself.

Figure 6:
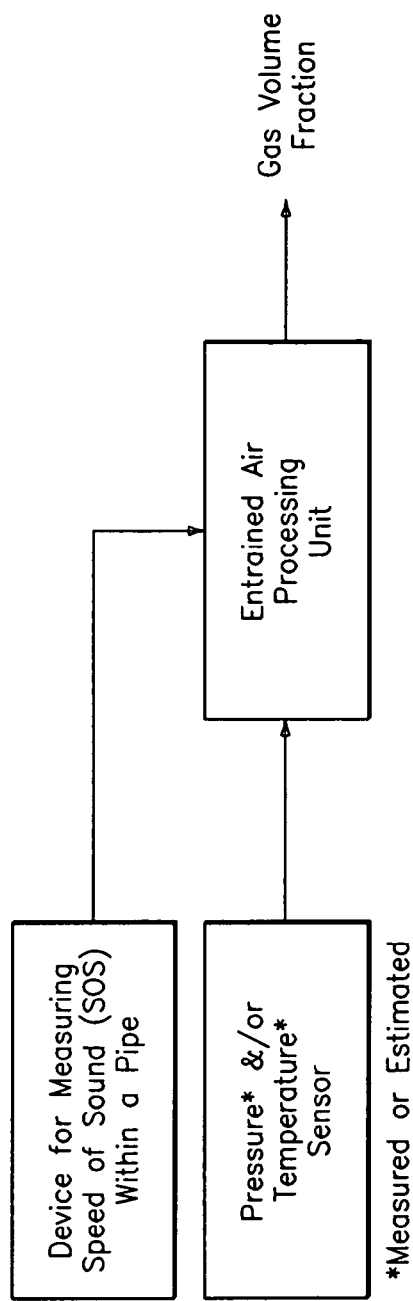
FIGS. 6 and 7 are block diagrams of the GVF Logic in accordance with the present invention.
Figure 7:
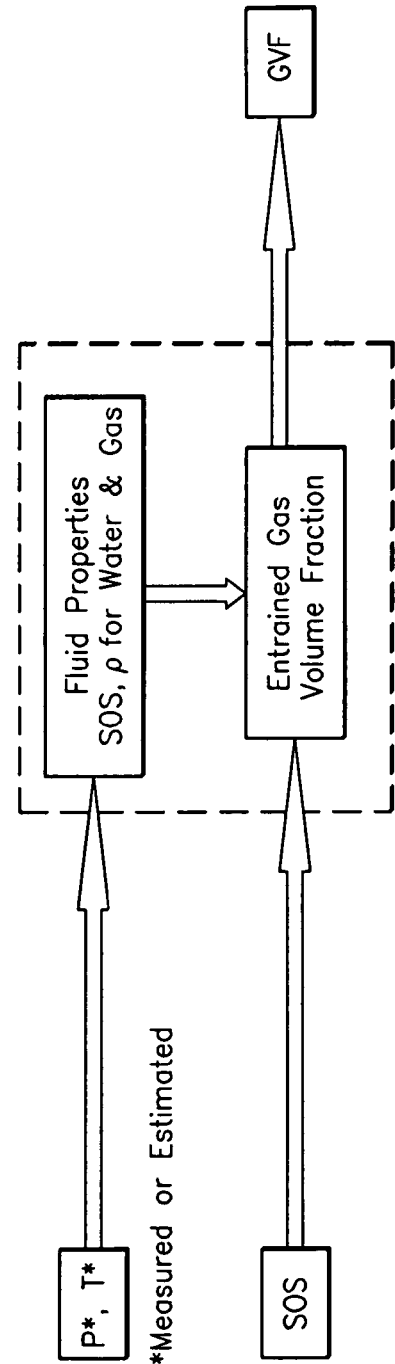

Generally, the processing unit 114 measures unsteady pressures created by acoustical disturbances propagating through the flow 102 to determine the speed of sound (SOS) propagating through the flow 102. Knowing the pressure and/or temperature of the flow 102 and the speed of sound of the acoustic disturbances or waves, as shown in FIG. 6 and FIG. 7, the processing unit 114 can determine the volumetric flow of the fluid 102, the consistency or composition of the fluid 102, the Mach number of the fluid 102, the average size of particles flowing through the fluid 102, the air/mass ratio of the fluid 102, and/or the percentage of entrained air within the mixture 102, such as that described in U.S. patent application Ser. No. 10/349,716, U.S. Publication No. 03-0154036, filed Jan. 23, 2003, U.S. patent application Ser. No. 10/376,427, filed Feb. 26, 2003, now U.S. Pat. No. 7,032, 432, and U.S. patent application Ser. No. 10/762,410, filed Jan. 21, 2004, now U.S. Pat. No. 7,062,976, which are all incorporated herein by reference.

As shown in FIG. 4, an apparatus 100 embodying the present invention has an array of at least two strain-based or pressure sensors 116, 118, located at two locations $x_1$, $x_2$ axially along the pipe 104 for sensing respective stochastic signals propagating between the sensors 116, 118 within the pipe 104 at their respective locations. Each sensor 116, 118 provides a signal indicating an unsteady pressure at the location of each sensor 116, 118, at each instant in a series of sampling instants. One should appreciate that the sensor array may include more than two pressure sensors 116, 118 as depicted by pressure sensors 120, 122 at locations $x_3$, $x_N$. The pressure generated by the acoustic waves 90 (see FIG. 5) may be measured through strained-based sensors and/or pressure sensors 116-122. The pressure sensors 116-122 provide analog pressure time-varying signals $P_1(t),P_2(t),P_3(t),P_N(t)$ to the signal processing unit 114.

Figure 8:
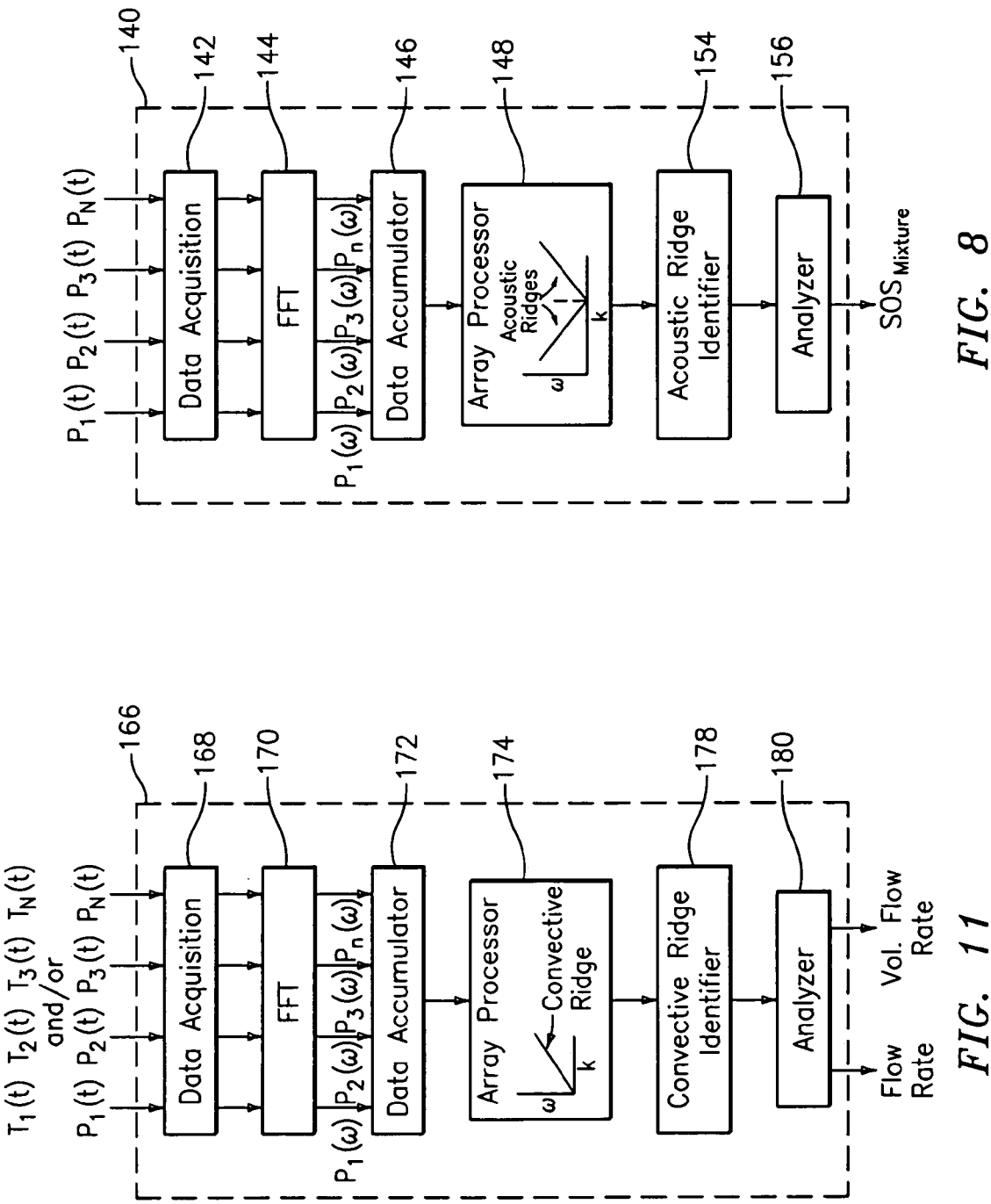
FIG. 8 is a schematic diagram of a speed of sound (SOS) logic of an array processor of a flow measuring apparatus in accordance with the present invention.

As shown in FIG. 8, the SOS Mixture Logic 140 includes a data acquisition unit 142 that digitizes the pressure signals $P_1(t)$-$P_N(t)$ associated with the acoustic waves 90 propagating through the pipe 104. An FFT logic 144 calculates the Fourier transform of the digitized time-based input signals $P_1(t)$-$P_N(t)$ and provides complex frequency domain (or frequency based) signals $P_1(\omega),P_2(\omega),P_3(\omega),P_N(\omega)$ indicative of the frequency content of the input signals.

A data accumulator 146 accumulates the signals $P_1(t)$-$P_N(t)$ from the sensors 116-122, and provides the data accumulated over a sampling interval to an array processor 148, which performs a spatial-temporal (two-dimensional) transform of the sensor data, from the x(t) domain to the k-ω domain, and then calculates the power in the k-ω plane, as represented by a k-ω plot, similar to that provided by the convective array processor shown in FIG. 11.

To calculate the power in the k-ω plane, as represented by a k-ω plot (see FIG. 9) of either the signals or the differenced signals, the array processor 148 determines the wavelength and as such the (spatial) wavenumber k, and also the (temporal) frequency and as such, the angular frequency ω, of various of the spectral components of the stochastic parameter. There are numerous algorithms available in the public domain to perform the spatial/temporal decomposition of the array of pressure sensors 116-122.

Specifically, the array processor 148 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi v$.

Figure 9:
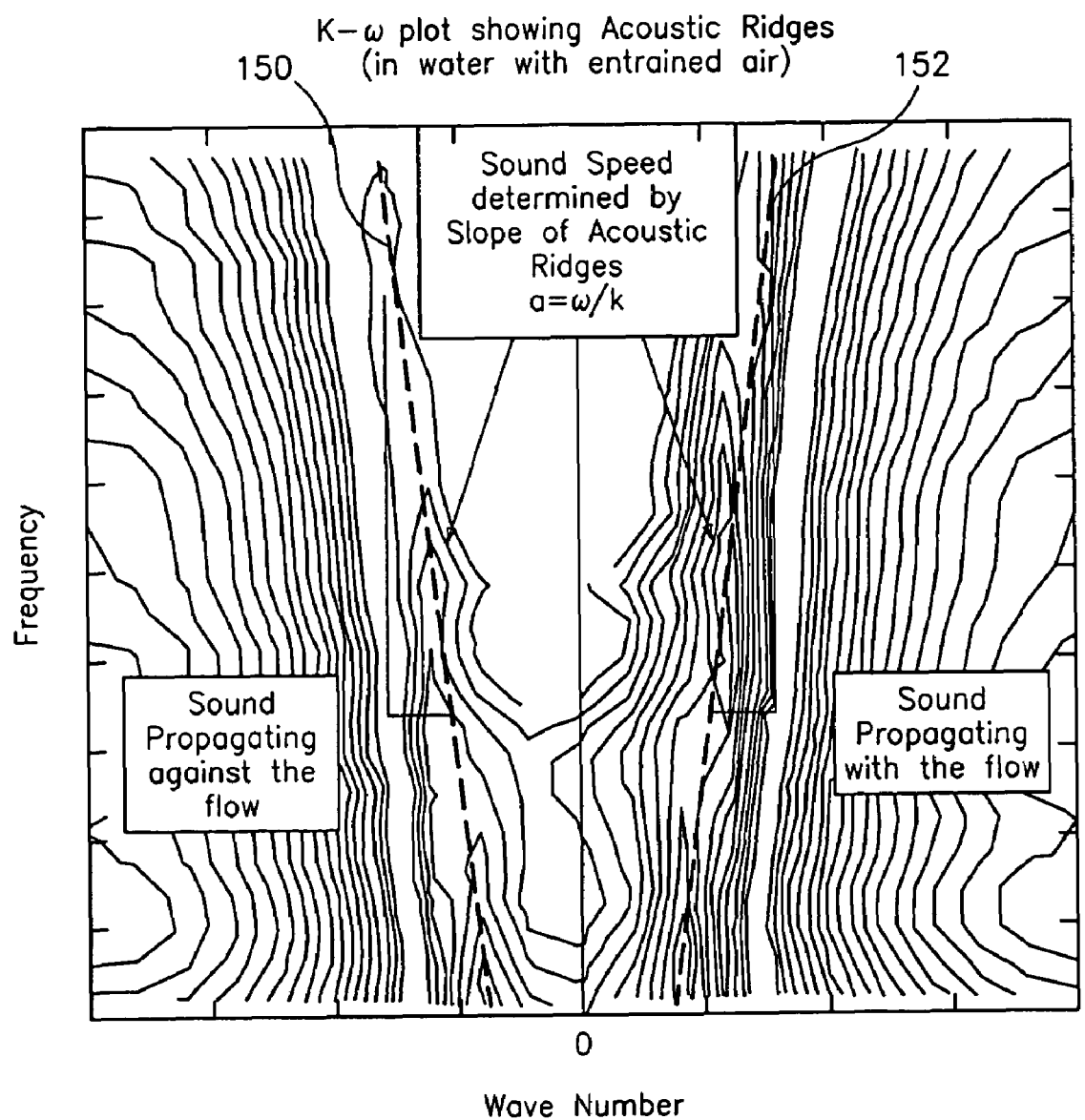
FIG. 9 a kω plot of data processed from an apparatus embodying the present invention that illustrates the slopes of a pair of acoustic ridges, in accordance with the present invention.

One such technique of determining the speed of sound propagating through the flow 102 involves using array processing techniques to define an acoustic ridge in the k-ω plane as shown in FIG. 9. The slope of the acoustic ridge is indicative of the speed of sound propagating through the flow 102. The speed of sound (SOS) is determined by applying sonar arraying processing techniques to determine the speed at which the one dimensional acoustic waves 90 propagate past the axial array of unsteady pressure measurements distributed along the pipe 104.

The apparatus 100 of the present invention measures the speed of sound (SOS) of one-dimensional sound waves 90 (see FIG. 5) propagating through the mixture 102 to determine the gas volume fraction of the mixture 102. It is known that sound propagates through various mediums at various speeds in such fields as SONAR and RADAR fields. The speed of sound propagating through the pipe 104 and flow 102 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; now U.S. Pat. No. 7,146,864, U.S. patent application Ser. No. 09/997,221, filed Nov. 28, 2001, now U.S. Pat. No. 6,587,798; U.S. patent application Ser. No. 10/007,749, filed Nov. 7, 2001, now U.S. Pat. No. 6,732,575, and U.S. patent application Ser. No. 10/762,410, filed Jan. 21, 2004, now U.S. Pat. No. 7,062,976, each of which are incorporated herein by reference.

In the case of suitable acoustic waves 90 being present in both axial directions, the power in the k-ω plane shown in a k-ω plot of FIG. 9 so determined will exhibit a structure that is called an acoustic ridge 150, 152 in both the left and right planes of the plot, wherein one of the acoustic ridges 150 is indicative of the speed of sound traveling in one axial direction and the other acoustic ridge 152 being indicative of the speed of sound traveling in the other axial direction.

The acoustic ridges 150, 152 represent the concentration of a stochastic parameter that propagates through the flow 102 and is a mathematical manifestation of the relationship between the spatial variations and temporal variations described above. Such a plot will indicate a tendency for k-ω pairs to appear more or less along a line 150, 152 with some slope, the slope indicating the speed of sound. The power in the k-ω plane so determined is then provided to an acoustic ridge identifier 154, which uses one or another feature extraction method to determine the location and orientation (slope) of any acoustic ridge 150. 152 present in the left and right k-ω plane. An analyzer 156 determines the speed of sound of the mixture 102 by using the slope of one of the two acoustic ridges 150, 152 or averaging the slopes of the acoustic ridges 150, 152.

As shown in FIGS. 1 and 4, the GVF logic provides output signals indicative of gas volume or void fraction of the mixture 102 in response to the measured speed of sound of the mixture 102. For example, to determine the gas volume fraction (or phase fraction), the GVF logic assumes a nearly isothermal condition for the flow 102. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}\hat{\;}2)$; Rg=gas density, rl=liquid density, $K_{eff}$=effective K (modulus of the liquid and pipewall), P=pressure, and $a_{meas}$=measured speed of sound.

Effectively,

Gas Volume Fraction$(GVF)=(-B+\text{sqrt}(B\hat{\;}2-4*A*C))/(2*A)$

Alternatively, the sound speed of a mixture 102 can be related to volumetric phase fraction ($\phi_i$) of the components and the sound speed (a) and densities ($\rho$) of the component through the Wood equation.

$$\frac{1}{\rho_{mix}a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves propagating within a mixture 102 contained within the pipe 104 exerts an unsteady internal pressure loading on the pipe 104. The degree to which the pipe 104 displaces as a result of the unsteady pressure loading influences the speed of propagation of the compression wave. The relationship among the infinite domain speed of sound and density of the mixture 102, the elastic modulus (E), thickness (t), and radius (R) of a vacuum-backed cylindrical conduit and the effective propagation velocity ($a_{eff}$) for one dimensional compression may be given by the following expression:

$$a_{eff} = \frac{1}{\sqrt{1/a_{mix\infty}^2 + \rho_{mix}\frac{2R}{Et}}} \quad (\text{eq 1})$$

Figure 10:
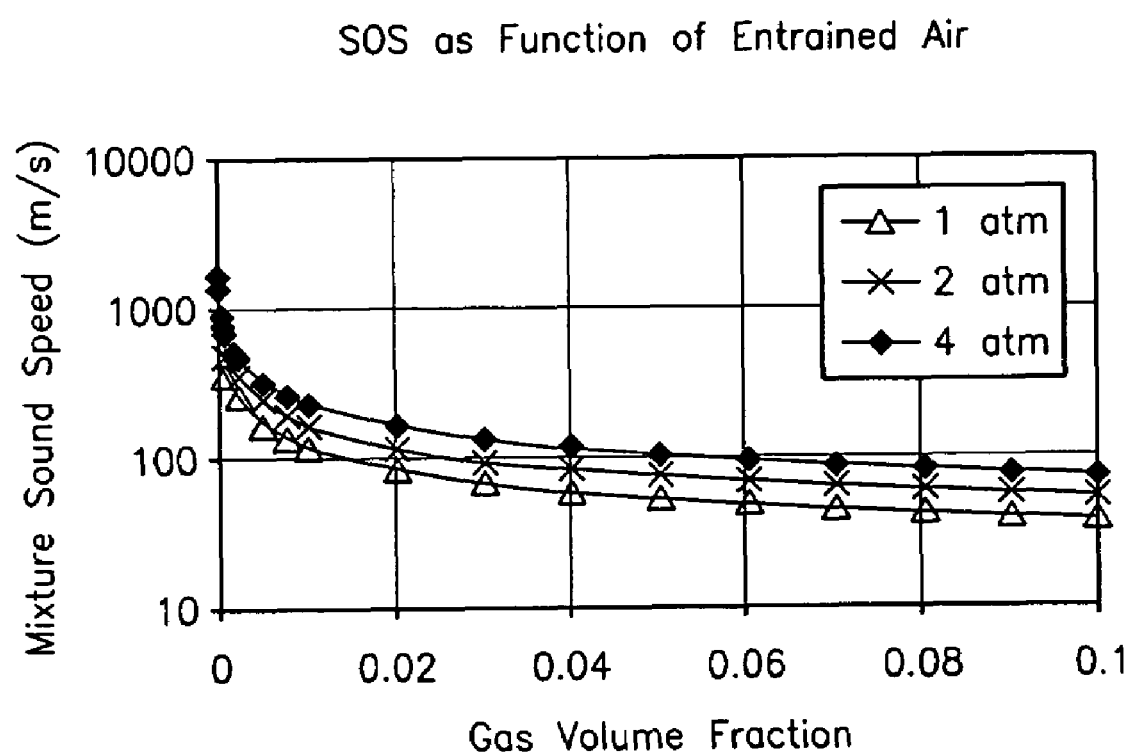
FIG. 10 is a plot of mixture sound speed as a function of gas volume fraction over a range of process pressures, in accordance with the present invention.

The mixing rule essentially states that the compressibility of a mixture ($1/(\rho a^2)$) is the volumetrically-weighted average of the compressibilities of the components. For gas/liquid mixtures 102 at pressure and temperatures typical of paper and pulp industry, the compressibility of the gas phase is orders of magnitudes greater than that of the liquid phase. Thus, the compressibility of the gas phase and the density of the liquid phase primarily determine mixture sound speed, and as such, it is necessary to have a good estimate of process pressure to interpret mixture sound speed in terms of the volumetric fraction of the entrained gas. The effect of process pressure on the relationship between sound speed and entrained air volume fraction is shown in FIG. 10.

Some or all of the functions within the processing unit 114 may be implemented in software (using a microprocessor or computer) and/or firmware, or may be implemented using analog and/or digital hardware, having sufficient memory, interfaces, and capacity to perform the functions described herein.

As shown in FIG. 4, the measurement apparatus 100 includes a sensing device 112 comprising an array of ultrasonic sensor units 124-130. Each sensor unit 124-130 comprises a pair of ultrasonic sensors 131, 132 one of which functions as a transmitter (Tx) 131 and the other as a receiver (Rx) 132. The sensor units 124-130 are spaced axially along the outer surface 134 of the pipe 104 having a process flow 102 propagating therein. The pair of sensors 131, 132 are diametrically disposed on the pipe 104 at predetermined locations along the pipe 104 to provide a through transmission configuration, such that the sensors 131, 132 transmit and receive an ultrasonic signal that propagates through the fluid 102 substantially orthogonal to the direction of the flow of the fluid 102 within the pipe 104. The ultrasonic measurement portion of the present invention is similar to that shown in U.S. Provisional Patent Application No. 10/756,977 filed on Jan. 13, 2004, which is incorporated herein by reference.

As shown in FIG. 1, each pair of ultrasonic sensors 131, 132 measures a transit time (i.e., time of flight (TOF), or phase modulation) of an ultrasonic signal propagating through the fluid 102 from the transmitting sensor 131 to the receiving sensor 132. The transit time measurement or variation is indicative of coherent properties that convect with the flow 102 within the pipe 104 (e.g., vortical disturbances, inhomogenieties within the flow 104, temperature variations, bubbles, particles, pressure disturbances), which are indicative of the velocity of the process flow 102. The ultrasonic sensors 124-130 may operate at any frequency, however, it has be found that the higher frequency sensors are more suitable for single phase fluids while lower frequency sensors are more suitable for multiphase fluids. The optimum frequency of the ultrasonic sensor 124-130 is dependent on the size or type of particle or substance propagating with the flow 102. For instance, the larger the air bubbles in an aerated fluid the lower the desirable frequency of the ultrasonic signal. Examples of frequency used for a flow meter embodying the present invention are 1 MHz and 5 MHz. The ultrasonic sensors 124-130 may also provide a pulsed, chirped or continuous signal through the fluid flow 102. An example of the sensors 131, 132 that may be used are Model no. 113-241-591, manufactured by Krautkramer.

An ultrasonic signal processor 162 fires the sensors 131 in response to a firing signal from the transmitter 114 and receives the ultrasonic output signals $S_1(t)$-$S_N(t)$ from the sensors 132. The ultrasonic signal processor 162 processes the data from each of the sensor units 124-130 to provide an analog or digital output signal $T_1(t)$-$T_N(t)$ indicative of the time of flight or transit time of the ultrasonic signal through the fluid 102. The ultrasonic signal processor 162 may also provide an output signal indicative of the amplitude (or attenuation) of the ultrasonic signals. One such signal processor is model no. USPC 2100 manufactured by Krautkramer Ultrasonic Systems. Measuring the amplitude of the ultrasonic signal is particularly useful and works best for measuring the velocity of a fluid 102 that includes a substance in the flow 102 (e.g., multiphase fluid or slurry).

The output signals ($T_1(t)$-$T_N(t)$) of the ultrasonic signal processor 162 are provided to the processor 114, which processes the transit time or modulation measurement data to determine the volumetric flow rate. The transit time or time of flight measurement is defined by the time it takes for an ultrasonic signal to propagate from the transmitting sensor 131 to the respective receiving sensor 132 through the wall of the pipe 104 and the fluid 102. The effect of the vortical disturbances (and/or other inhomogenities within the fluid 102) on the transit time of the ultrasonic signal is to delay or speed up the transit time. Therefore, each sensing unit 124-130 provides a respective output signal $T_1(t)$-$T_N(t)$ indicative of the variations in the transit time of the ultrasonic signals propagating orthogonal to the direction of the fluid 102. The measurement is derived by interpreting the convecting coherent property and/or characteristic within the process piping 104 using at least two sensor units 124, 126. The ultrasonic sensors 124-126 may be "wetted" or clamped onto the outer surface 134 of the pipe 104 (e.g. contact or non-contact sensor).

In one example, the flow meter 100 measures the volumetric flow rate by determining the velocity of vortical disturbances or "eddies" 164 (see FIG. 5) propagating with the flow 102 using the array of ultrasonic sensors 124-130. The flow meter 100 measures the velocities associated with unsteady flow fields created by the vortical disturbances or "eddies" 164 and other inhomogenities to determine the velocity of the flow 102. The ultrasonic sensor units 124-130 measure the transmit time $T_1(t)$-$T_N(t)$ of the respective ultrasonic signals between each respective pair of sensors 131, 132, which vary due to the vortical disturbances as these disturbances convect within the flow 102 through the pipe 104 in a known manner. Therefore, the velocity of these vortical disturbances is related to the velocity of the flow 102 and hence the volumetric flow rate may be determined, as will be described in greater detail hereinafter. The volumetric flow is determined by multiplying the velocity of the fluid 102 by the cross-sectional area of the pipe 104.

The Flow Logic 166 of the processing unit 112 processes the ultrasonic signals as shown in FIG. 11. The Flow Logic 166 receives the ultrasonic signals from the array of sensors 124-130. A data acquisition unit 168 (e.g., A/D converter) converts the analog signals to respective digital signals. The digitized signals are provided to Fast Fourier Transform (FFT) logic 170. The FFT logic 170 calculates the Fourier transform of the digitized time-based input signals $T_1(t)$-$T_N(t)$ and provides complex frequency domain (or frequency based) signals $T_1(\omega)$, $T_2(\omega)$, $T_3(\omega)$, $T_N(\omega)$ indicative of the frequency content of the input signals. Instead of FFT's, any other technique for obtaining the frequency domain characteristics of the signals $T_1(t)$-$T_N(t)$, may be used. For example, the cross-spectral density and the power spectral density may be used to form a frequency domain transfer functions (or frequency response or ratios) discussed hereinafter.

One technique of determining the convection velocity of the turbulent eddies 164 within the process flow 102 (see FIG. 5) involves characterizing a convective ridge of the resulting unsteady pressures using an array of sensors or other beam forming techniques, similar to that described in U.S. patent application Ser. No. 10/007,736 filed Nov. 8, 2001 now U.S. Pat. No. 6 889,562 and U.S. patent application, Ser. No. 09/729,994, filed Dec. 4, 2000, now U.S. Pat. No. 6,609,069, which are incorporated herein by reference.

A data accumulator 172 accumulates the frequency signals $T_1(\omega)$-$T_N(\omega)$ over a sampling interval, and provides the data to an array processor 174, which performs a spatial-temporal (two-dimensional) transform of the sensor data, from the x(t) domain to the k-ω domain, and then calculates the power in the k-ω plane, as represented by a k-ω plot.

The array processor 174 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

where u is the convection velocity (flow velocity). A plot of k-ω pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies 164, but rather a continuum of possibly overlapping events forming a temporally stationary, essentially white process over the frequency range of interest. In other words, the convective eddies 164 are distributed over a range of length scales and hence temporal frequencies.

To calculate the power in the k-ω plane, as represented by a k-ω plot (see FIG. 12) of either the signals, the array processor 174 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 124-130.

The present invention may use temporal and spatial filtering to precondition the signals to effectively filter out the common mode characteristics $P_{common\ mode}$ and other long wavelength (compared to the sensor spacing) characteristics in the pipe 104 by differencing adjacent sensors and retain a substantial portion of the stochastic parameter associated with the flow field and any other short wavelength (compared to the sensor spacing) low frequency stochastic parameters.

Figure 12:
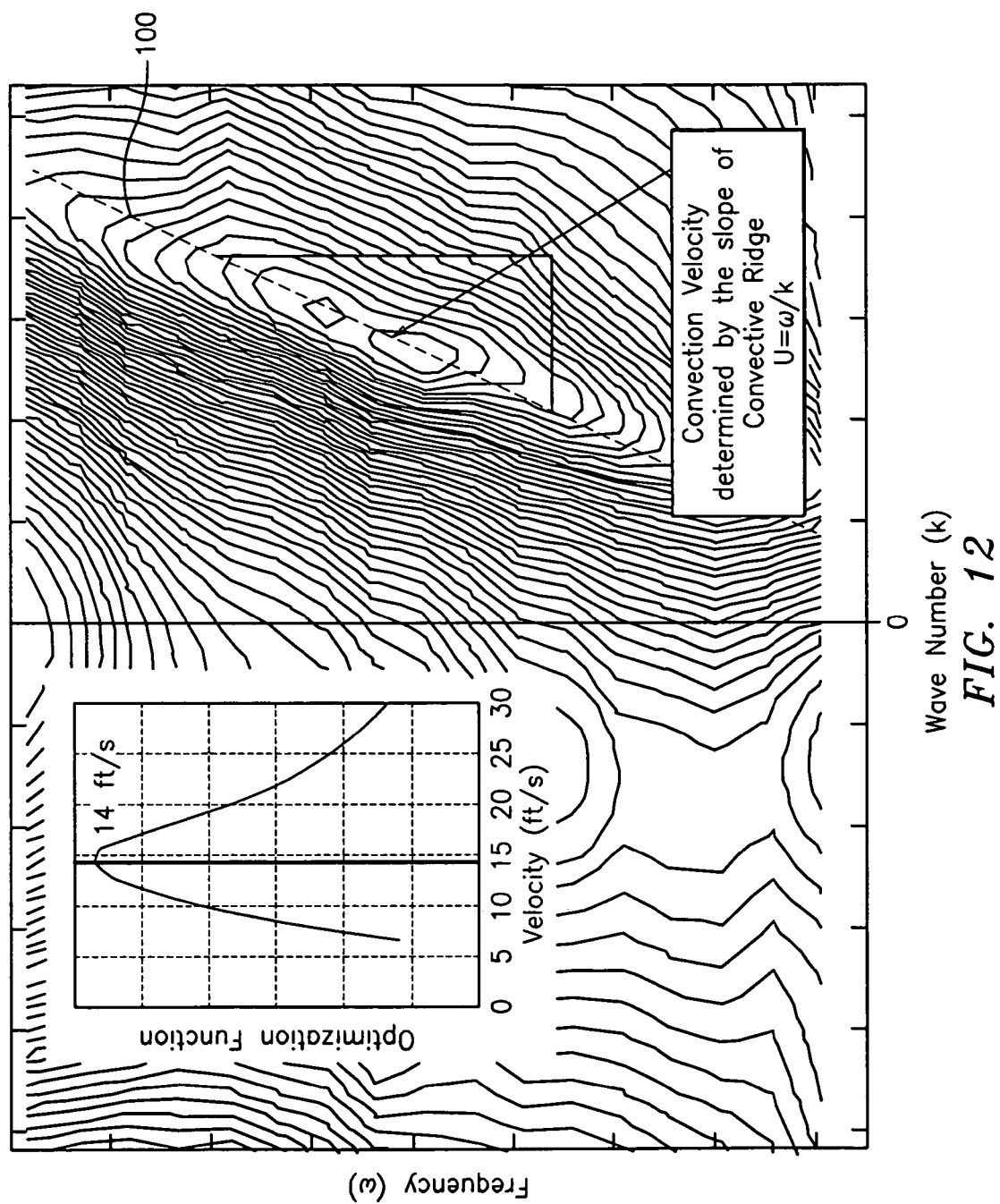
FIG. 12 a kω plot of data processed from an apparatus embodying the present invention that illustrates the slope of a convective ridge, and a plot of the optimization function of the convective ridge, in accordance with the present invention.

In the case of suitable turbulent eddies 164 (see FIG. 5) being present, the power in the k-ω plane shown in a k-ω plot of FIG. 12 shows a convective ridge 176. The convective ridge represents the concentration of a stochastic parameter that convects with the flow 102 and is a mathematical manifestation of the relationship between the spatial variations and temporal variations described above. Such a plot will indicate a tendency for k-ω pairs to appear more or less along a line 176 with some slope, the slope indicating the flow velocity.

Once the power in the k-ω plane is determined, a convective ridge identifier 178 uses one or another feature extraction method to determine the location and orientation (slope) of any convective ridge 176 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 178 provides information about the different trial convection velocities, information referred to generally as convective ridge information.

An analyzer 180 examines the convective ridge information including the convective ridge orientation (slope).

Assuming that the straight-line dispersion relation is given by k=ω/u, the analyzer 180 determines the flow velocity, Mach number and/or volumetric flow. The volumetric flow may be determined by multiplying the cross-sectional area of the inside of the pipe 104 with the velocity of the process flow 102.

The watercut of the process flow 102 may be determined by using the output of at least one of the sensors 124-130 of the ultrasonic flow meter 108. While an ultrasonic sensor 124-130 of the ultrasonic flow meter 108 is used to determine the watercut of the flow 102, it is contemplated that a separate ultrasonic sensor may also be used to determine the watercut. A separate ultrasonic sensor for measuring watercut would allow the sensor to transmit an ultrasonic signal at different frequencies to ensure the ultrasonic sensor for watercut is operating at a freguency greater than the bubble resonant frequency.

Figure 13:
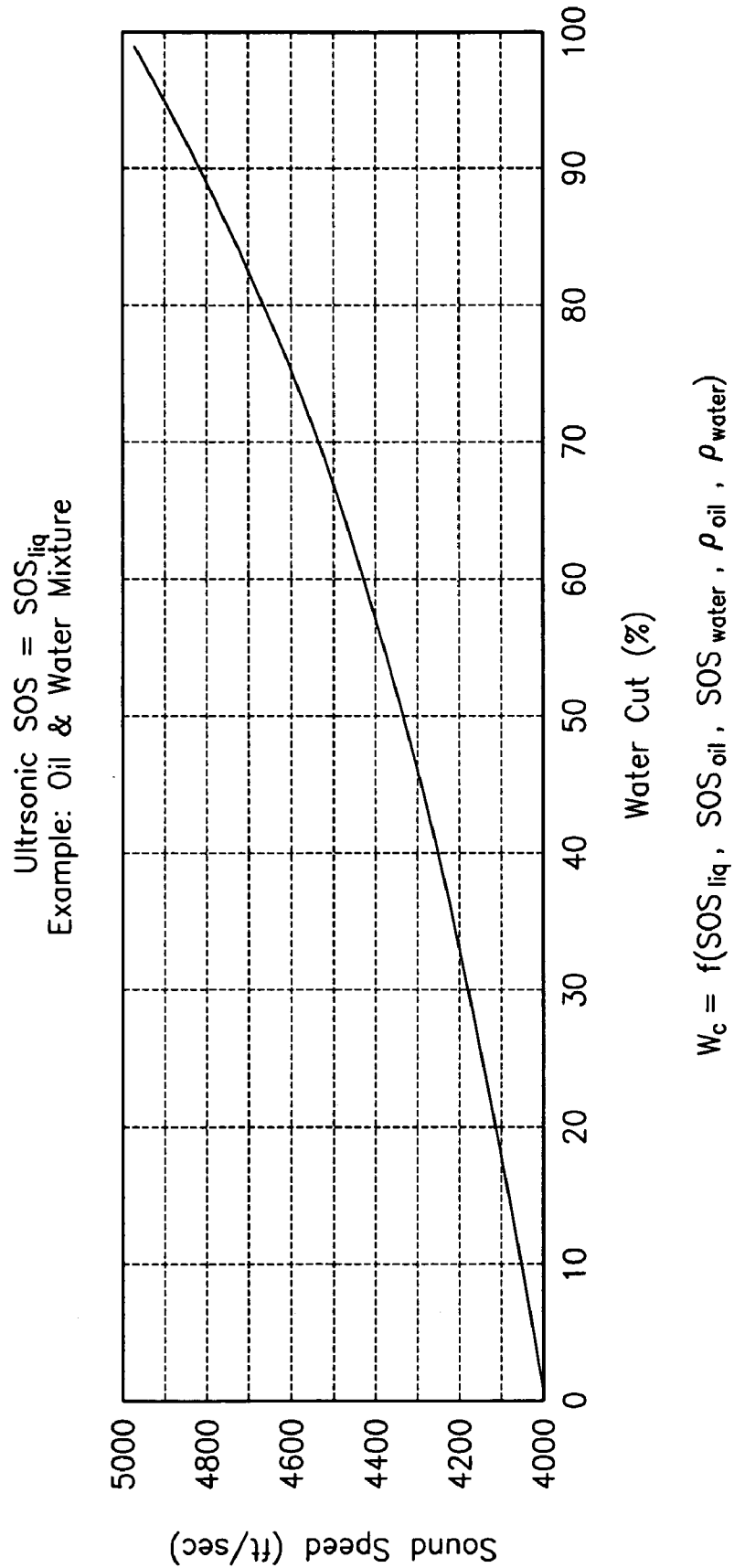
FIG. 13 is a plot of the speed of sound of the liquid as a function of the volume fraction of the water in the multiphase flow in accordance with the present invention.

The SOS Liquid Logic converts the measured transit time of the ultrasonic signal to a signal indicative of the speed of sound of the liquid component of the mixture 102. The frequency of the ultrasonic signal propagating through the fluid flow 102 is greater than the bubble resonant frequency such that entrained gas does not affect the ultrasonic signal. Knowing the SOS of the liquid portion of the fluid flow 102, the water cut of the fluid flow 102 can be determined. The water cut is a function of the SOS of the liquid component of the mixture 102, the SOS of the oil, SOS of the water, the density of the oil, and the density of the water. Knowing the SOS and density of the oil and water, the relationship between the water cut of the flow 102 and the SOS of the liquid component of the mixture 102, the waster cut can be determined. As shown in FIG. 13, this relationship is illustrated in the plot of SOS of the liquid component of the mixture 102 v. water cut, and therefore, knowing the SOS of the liquid component of the mixture 102, the water cut may be determined.

The water cut is defined as:

$$W_c = \phi_w / (\phi_w + \phi_o)$$

wherein $\phi_w$ is the phase fraction of the water component of the fluid flow, and $\phi_o$ is the phase fraction of the oil component of the fluid flow.

Further the phase fraction of the fluid flow can be characterized as:

$$1 = \phi_w + \phi_o + \phi_g$$

wherein $\phi_w$ is the phase fraction of the water component of the fluid flow, $\phi_o$ is the phase fraction of the oil component of the fluid flow, and $\phi_g$ is the phase fraction of the gas component of the fluid flow.

The present invention measures the water cut ($W_c$) and the GVF ($\phi_g$), as described hereinbefore. The processor 114 using the above relationships (formulas) may determined the phase fractions of the water ($\phi_w$) and oil ($\phi_o$) (i.e., composition of the fluid flow 102).

The processor 114 may then (knowing the phase fraction of each component of the fluid) determine the volumetric flow rate of each component using the following formula:

$$Q_p = \phi_p (U)(A)$$

Wherein $Q_p$ is the volumetric flow rate of phase (component), $\phi_p$ is the phase fractio of the phase; and U is the velocity of the fluid flow, and A is the cross-sectional area of the pipe.

While the sonar-based flow meter 100 using an array of sensors 124-130 to measure the speed of sound of an acoustic wave 90 propagating through the mixture is shown and described, one will appreciate that any means for measuring the speed of sound of the acoustic wave 90 may be used to determine the entrained gas volume fraction of the mixture/fluid 102 or other characteristics of the flow 102 described hereinbefore.

While each of the ultrasonic sensor units 124-130 of FIG. 1 comprises a pair of ultrasonic sensors (transmitter and receiver) 131, 132 diametrically-opposed to provide through transmission, the present invention contemplates that one of the ultrasonic sensors 131, 132 of each sensor unit 124-130 may be offset axially such that the ultrasonic signal from the transmitter sensor 131 has an axial component in its propagation direction.

The present invention also contemplates that the sensor units 124-130 of the sensing device 112 may be configured in a pulse/echo configuration. In this embodiment, each sensing unit 124-130 comprises one ultrasonic sensor that transmits an ultrasonic signal through the pipe 104 wall and fluid 102 substantially orthogonal to the direction of flow and receives a reflection of the ultrasonic signal reflected back from the wall 104 of the pipe to the ultrasonic sensor.

Moreover, the sensing device 112 may be configured to function in a pitch and catch configuration. In this embodiment, each sensor unit 124-130 comprises a pair of ultrasonic sensors (transmitter, receiver) 131, 132 disposed axially along the pipe 104 to be disposed on the same side of the pipe 104 at a predetermined distance apart. Each transmitter sensor 131 provides an ultrasonic signal at a predetermined angle into the flow 102. The ultrasonic signal propagates through the fluid 102 and reflects off of the inner surface of the pipe 104 and reflects the ultrasonic signal back through the fluid 102 to the respective receiver sensor 132.

As shown in FIG. 1, while the ultrasonic sensor portion comprises an array of ultrasonic sensor units 124-130 (see FIG. 5), the present invention contemplates that any ultrasonic flow meter 108 or sensing portion may be used. The ultrasonic flow meter 108 may be any meter within any of the three classes of flow meters that utilize ultrasonic transducers, which include transit time ultrasonic flow meters (TTUF), doppler ultrasonic flow meters (DUF), and cross correlation ultrasonic flow meters (CCUF).

The ultrasonic sensor portion may be any known ultrasonic flow meter 108, such as U.S. Pat. No. 2,874,568; U.S. Pat. No. 4,004,461; U.S. Pat. No. 6,532,827; U.S. Pat. No. 4,195,517; U.S. Pat. No. 5,856,622; and U.S. Pat. No. 6,397,683, which are all incorporated herein by reference.

The array-based flow meter 108 is similar to that described in U.S patent application, Ser. No. 10/007,749 filed Nov. 7, 2001 , now U.S. Pat. No. 6,732,575, U.S patent application, Ser. No. 10/007,736 filed Nov. 8, 2001 , now U.S. Pat. No. 6,889,562, U.S. Pat. No. 6,587,798, filed on Nov. 28, 2001, U.S. Provisional Patent Application, Ser. No. 60/359,785 filed Feb. 26, 2002 U.S Provisional Patent Application, Ser. No. 60/425,436 filed Nov. 12, 2002 , U.S. patent application Ser. No. 09/729,994, filed Dec. 4, 2000 , now U.S. Pat. No. 6,609,069, and U.S. patent application, Ser. No. 10/875,857 filed Jun. 24, 2004, now U.S. Pat. No. 7,127,360, which are all incorporated herein by reference.

While a single array processor 114 is shown to receive and process input signals from the pressure sensors 116-122 and the ultrasonic sensors 124-130, the present invention contemplates that an array processor may be dedicated to each of the array of pressure sensors 116-122 and the array of ultra-sonic sensors 124-130. Moreover, while data acquisition units 142, 168, FFT logic 144, 170, data accumulators 146, 172, array processors 148, 174 and ridge identifiers 154, 178 are shown as separate elements or separate software/processing routines, one will appreciate that each of these elements may be common and able to process the data associated with both the pressure signals associated with the speed of sound and the pressures that convect with the process flow 102.

Figure 14:
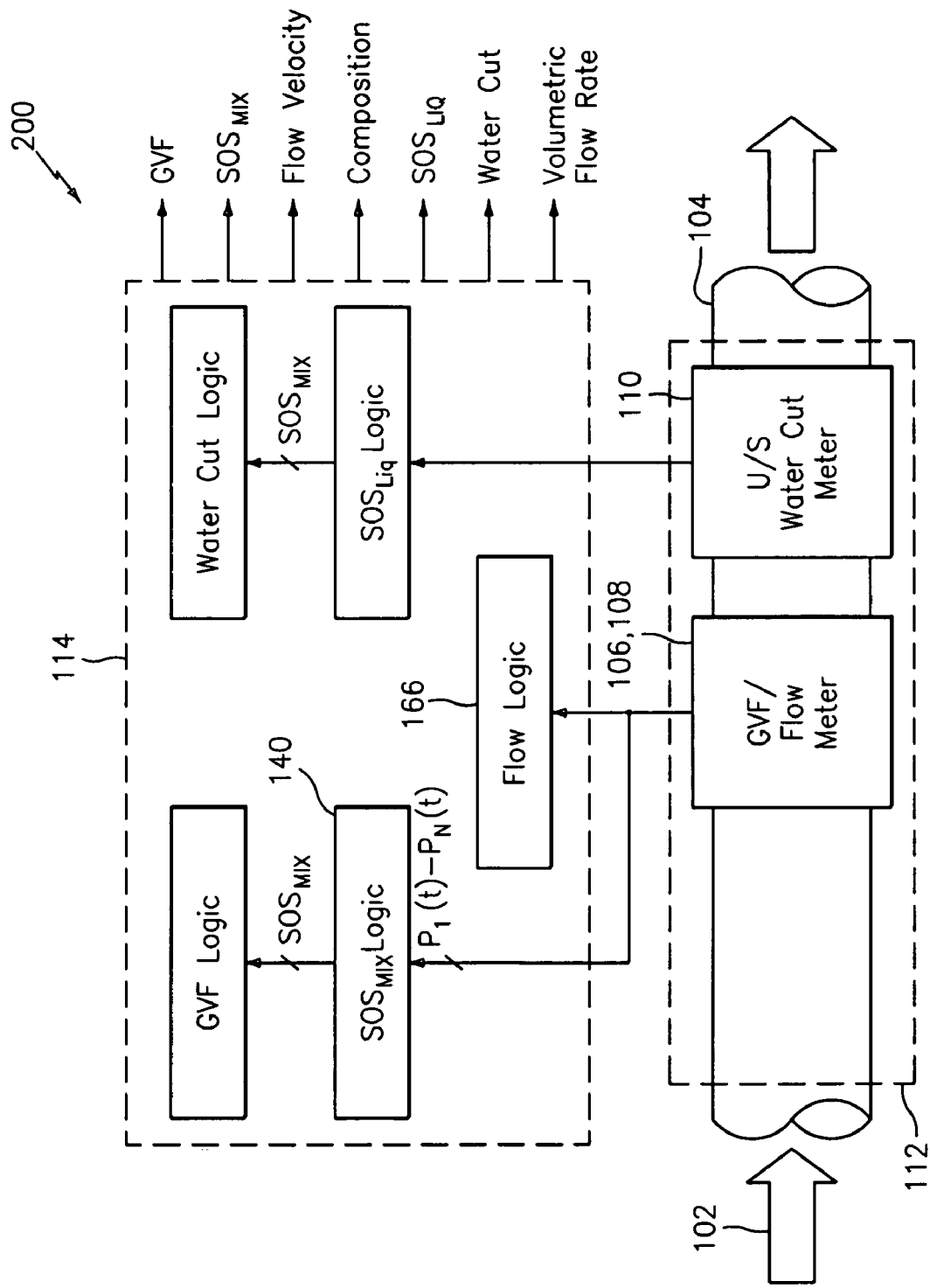
FIG. 14 is a block diagram of another embodiment of a flow measurement apparatus having an array of strain-based sensors and an ultrasonic sensors for measuring parameters of a multiphase flow in accordance with the present invention.

FIG. 14 illustrates a block diagram of a flow measurement apparatus 200 similar to the apparatus of FIG. 1 that includes a sensing device (sensor head) 112 mounted to a pipe 104 and a processing unit or array processor (transmitter) 114. The apparatus 200 functions as a GVF meter 106, a flow meter 108, and a watercut meter 110. In this embodiment, the sensor head 112 for the GVF meter 106 functions as the sensor head 112 for both the GVF meter 106 and flow meter 108 of FIG. 1. The processing of all the data is similar to that described hereinbefore. Like reference numbers are the same elements and function in the same manner as that described herein before.

Figure 15:
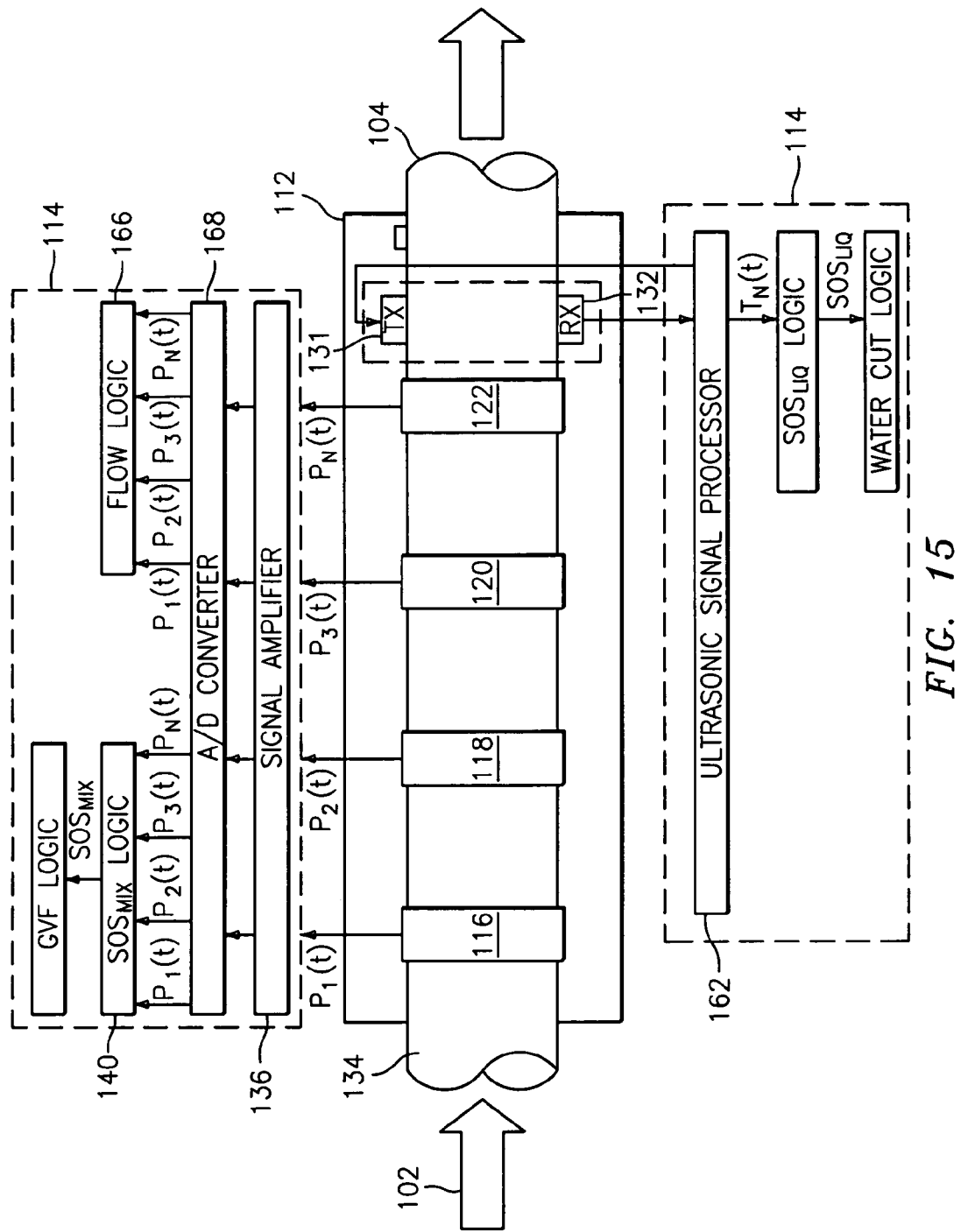
FIG. 15 is a schematic diagram of a flow measurement apparatus of FIG. 14 having an array of strain-based sensors and an array of ultrasonic sensors for measuring parameters of a multiphase flow.

Referring to FIG. 15, the sensor head 112 includes an array of strained-based or pressure sensors 116-122. The signals provided by the pressure sensors 116-122 are processed to determine the gas volume (or void) fraction of the flow 102, the velocity of the flow 102, the volumetric flow rate, and the speed of sound of the mixture (i.e., flow) 102. The combination GVF/flow meter, in accordance with the present invention, can determine the speed at which sound (i.e., acoustic wave 90 in FIG. 5) propagates through the fluid flow 102 within the pipe 104 to measure the speed of sound of the mixture 102 and the gas void (or volume) fraction of the flow 102. The GVF/flow meter may also determine the speed at which pressure disturbances (e.g., vortical disturbances) propagate through the pipe 104 to determine the velocity of the fluid flow 102. The pressure disturbances may be in the form of vortical disturbances 164 (e.g., turbulent eddies FIG. 5) or other pressure disturbances that convect (or propagate) with the flow 102.

As suggested and further described in greater detail hereinafter, the apparatus 200 has the ability to measure the speed of sound (SOS) and flow rate (or velocity) using one or both of the following techniques using the same array of pressure sensors 116-122 described herein below:

1) Determining the speed of sound of acoustical disturbances or sound waves propagating through the flow 102 using the array of pressure sensors 116-122, and/or
2) Determining the velocity of pressure disturbances (e.g., vortical eddies 164) propagating through the flow 102 using the array of pressure sensors 116-122.

These techniques are similar to what was taught and described hereinbefore in reference to FIGS. 8 and 11, respectively. Also, the processing relating to the watercut meter 110 is similar to that described herein before.

One skilled in the art should appreciate that the water cut meter 110 may also be used as a stand alone meter to enable a user to measure the water cut of a multiphase fluid flow 102 having entrained air.

The pressure sensors 116-122 and the ultrasonic sensors 124-130 shown in the apparatus 100, 200 in FIGS. 4 and 15, respectively, may be clamp-on, non-wetted sensors. These clamp-on sensors allow the apparatus 100, 200 to be retro fit onto pipes 104 without having to shut down the system. The apparatus 100, 200 also would not interfere with the fluid flow 102 and not create any back pressure of the fluid flow 102. Another advantage of the non-wetted, clamped on sensors is that corrosion or scaling does not interfere with the sensors.

In one embodiment as shown in FIGS. 4 and 15, each of the pressure sensors 116-122 may include a piezoelectric film attached to a unitary multi-band strap to measure the unsteady pressures of the flow 102 using either technique described hereinbefore. The piezoelectric film sensors 116-122 may be mounted onto a unitary substrate or web which may be mounted or clamped onto the outer surface 132 of the pipe 104, which will be described in greater detail hereinafter.

The piezoelectric film sensors 116-122 may include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors 116-122 can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc. While the piezoelectric film material is provided substantially the length of the band, and therefore the circumference of the pipe 104, the present invention contemplates that the piezoelectric film material may be disposed along a portion of the band of any length less than the circumference of the pipe 104.

Piezoelectric film ("piezoflim"), like piezoelectric material, is a dynamic material that develops an electrical charge proportional to a change in mechanical stress. Consequently, the piezoelectric material measures the strain induced within the pipe 104 due to unsteady or stochastic pressure variations (e.g., vortical and/or acoustical) within the process flow 102. Strain within the pipe 104 is transduced to an output voltage or current by the attached piezoelectric sensor 116-122. The piezoelectrical material or film maybe formed of a polymer, such as polarized fluoropolymer, polyvinylidene fluoride (PVDF). The piezoelectric film sensors are similar to that described in U.S. patent application Ser. No. 10/712,818, filed Nov. 12, 2003 and U.S. patent application Ser. No. 10/795,111, filed Mar. 4, 2004, now U.S. Pat. No. 7,146,864 which are incorporated herein by reference. The advantages of this clamp-on technique using piezoelectric film include non-intrusive flow rate measurements, low cost and measurement techniques that require no excitation source. One should appreciate that the sensor(s) 116-122 may be installed or mounted to the pipe 104 as individual sensors 116-122 or all of the sensors 116-122 may be mounted as a single unit as shown in FIGS. 4 and 15.

The pressure sensors 116-122 of FIG. 4 described herein may be any type of sensor, capable of measuring the unsteady (or ac or dynamic) pressures or parameters that convect with the flow 102 within the pipe 104, such as piezoelectric, optical, capacitive, resistive (e.g., Wheatstone bridge), accelerometers (or geophones), velocity measuring devices, displacement measuring devices, ultra-sonic devices, etc. If optical pressure sensors are used, the sensors 116-122 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat No. 6,016,702, and in U.S. patent application, Ser. No. 10/224,821, entitled "Non-Intrusive Fiber Optic Pressure Sensor for Measuring Unsteady Pressures within a Pipe", now U.S. Pat. No. 6,959,604, which are incorporated herein by reference. In an embodiment of the present invention that utilizes fiber optics as the pressure sensors 116-122, the pressure sensors 116-122 may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 116-122 and it may measure the unsteady (or dynamic or ac) pressure variations inside of the pipe 104 by measuring the pressure levels inside of the pipe 104. These sensors 116-122 may be ported within the pipe 104 to make direct contact with the process flow 102. In an embodiment of the present invention, the sensors 116-122 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems.

It is also within the scope of the present invention that any strain sensing technique may be used to measure the variations in strain in the pipe 104, such as highly sensitive piezoelectric, electronic or electric, strain gages and piezo-resistive strain gages attached to the pipe 104. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 104. The axial placement of and separation distance $\Delta X_1$, $\Delta X_2$ between the strain sensors 116-122 are determined as described herein above.

The information/measurement provided by the present invention may be used to monitor flow characteristic flowing with the pipe, to control a process, and to diagnose problems in the process. The user also retrieves the data stored in the processor via an input/output device/ports.

It is also within the scope of the present invention that any other strain sensing technique may be used to measure the variations in strain in the pipe 104, such as highly sensitive piezoelectric, electronic or electric, strain gages attached to or embedded in the pipe 104.

While the description has described the apparatus 100, 200 as a single meter that measures the GVF, Flow and watercut, each function may be separated into individual meters for measuring GVF, flow and watercut.

While the embodiments of the present invention include clamp on sensors or devices, one will appreciate that the sensors or devices may be ported or wetted to be in contact with the fluid flow 102.

The present invention further contemplates that a fluid mixing device, similar to that commonly know in the art, may be disposed prior to (or upstream of the flow) sensors to provide a well mixed fluid. A well mixed fluid assures minimal or no slippage between the liquid phase and the gas phase. Slippage is defined as a difference of velocity between the liquid phase and gas phase of the fluid flow 102.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An apparatus for determining a characteristic of a fluid flowing within a pipe, the device comprising:
at least one first sensing device, wherein said at least one first sensing device is associated with the pipe, such that said at least one first sensing device senses a low-frequency component of the fluid and generates first sensor data responsive to said low-frequency component of the fluid;
at least one second sensing device, wherein said at least one second sensing device is associated with the pipe such that said at least one second sensing device senses a high-frequency component of the fluid and generates second sensor data responsive to said high-frequency component of the fluid; and
a processing device, wherein said processing device is communicated with said at least one first sensing device and said at least one second sensing device to receive and process said first sensor data and said second sensor data to generate fluid data responsive to a characteristic of the fluid.

2. The apparatus of claim 1, wherein said characteristic of the fluid is at least one of a Gas Volume Fraction (GVF), a volumetric flow rate and a water cut value.

3. The apparatus of claim 1, wherein said at least one first sensing device generates first sensor data responsive to the speed of sound through the fluid.

4. The apparatus of claim 1, wherein the fluid includes a liquid phase comprising water and wherein said at least one second sensing device generates second sensor data responsive to at least one of the flow rate of the fluid and the speed of sound through said water.

5. The apparatus of claim 1, wherein said at least one first sensing device includes a plurality of first sensing devices, wherein said plurality of first sensing devices are axially distributed along the pipe.

6. The apparatus of claim 1, wherein said at least one second sensing device includes a plurality of second sensing devices, wherein said plurality of second sensing devices are axially distributed along the pipe.

7. The apparatus of claim 1, wherein said at least one second sensing device includes a transmitting device and a receiving device.

8. The apparatus of claim 7, wherein said transmitting device and said receiving device are disposed on diametrically opposing sides of the pipe.

9. The apparatus of claim 1, wherein the apparatus includes a fastening device for removably and securely associating the apparatus with an external portion of the pipe, wherein the fastening device is configured for easy removal and installation of the apparatus.

10. A method for determining a characteristic of a fluid flowing within a pipe, the method comprising:
generating Speed of Sound data responsive to the speed of sound within at least a portion of the fluid for at least one of a first frequency and a second frequency;
sensing the convective velocity of pressure fields created by the fluid and generating convective data responsive to the convective velocity of the pressure fields; and
processing said Speed of Sound data and said convective data to determine the characteristic of the fluid.

11. The method of claim 10, wherein the characteristic of the fluid is at least one of a Watercut value, a Gas Volumetric Fraction and a volumetric flow rate.

12. The method of claim 10, wherein said first frequency is less than about 1 KHz and wherein said second frequency is greater than about 100 KHz.

13. The method of claim 10, wherein said generating includes passively monitoring the fluid for sound waves having said first frequency.

14. The method of claim 10, wherein said generating further includes introducing a sound wave into the fluid on one side of the pipe such that the sound wave travels through the fluid in a direction orthogonal to the direction of flow of the fluid.

15. The method of claim 14, wherein said generating further includes sensing said sound wave by receiving said sound wave with a sensing device after said sound wave has traversed the fluid.

16. The method of claim 10, wherein said generating further includes introducing a sound wave into the fluid and sensing said sound wave by receiving said sound wave with a sensing device after said sound wave has traversed the fluid.

17. The method of claim 10, wherein said processing includes processing at least one of said Speed of Sound data for said first frequency, said Speed of Sound data for said second frequency and said convective data to determine at least one of a Watercut value, a Gas Volumetric Fraction and a volumetric flow rate.

18. An apparatus for determining the water cut value of a multiphase fluid flowing within a pipe, the device comprising:
   a transmitting device configured to introduce a high-frequency acoustic signal into the fluid;
   a receiving device, wherein said receiving device is configured to receive said high-frequency acoustic signal after said high-frequency acoustic signal has traversed at least a portion of the fluid, wherein at least one of said transmitting device and said receiving device generates sensor data responsive to said received high-frequency acoustic signal; and
   a processing device, wherein said processing device is communicated with at least one of said transmitting device and said receiving device to receive and process said sensor data to determine the water cut value of the fluid.

19. The apparatus of claim 18, wherein said high-frequency acoustic signal is an acoustic wave having a frequency of greater than about 100 KiloHertz into the fluid.

20. The apparatus of claim 19, wherein said sensor data is analog data and wherein said processing device generates digital data responsive to said analog data and processes said digital data to generate the water cut value.

21. A method for determining the water cut value of a fluid flowing through a pipe, the method comprising:
   introducing an acoustic wave having a predetermined frequency into the fluid;
   after said acoustic wave has traversed at least a portion of the fluid, receiving said acoustic wave and generating sensor data responsive at least in part to said received acoustic wave; and
   processing said sensor data to determine the water cut value of the fluid.

22. The method of claim 21, wherein said predetermined frequency is greater than about 100 KiloHertz.

23. The method of claim 21, wherein said introducing includes directionally introducing said acoustic wave into the fluid such that said acoustic wave traverses the fluid in a direction substantially orthogonal to the direction of flow of the fluid.

* * * * *